US012343538B2

(12) United States Patent
Moffitt et al.

(10) Patent No.: US 12,343,538 B2
(45) Date of Patent: *Jul. 1, 2025

(54) LINKING AND CONCURRENT STEERING OF MULTIPLE POLE CONFIGURATIONS IN A SPINAL CORD STIMULATION SYSTEM

(71) Applicant: Boston Scientific Neuromodulation Corporation, Valencia, CA (US)

(72) Inventors: Michael A. Moffitt, Solon, OH (US); Que T. Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/507,961

(22) Filed: Nov. 13, 2023

(65) Prior Publication Data

US 2024/0082579 A1 Mar. 14, 2024

Related U.S. Application Data

(63) Continuation of application No. 17/649,767, filed on Feb. 2, 2022, now Pat. No. 11,850,426, which is a continuation of application No. 16/774,720, filed on Jan. 28, 2020, now Pat. No. 11,273,309.

(60) Provisional application No. 62/802,982, filed on Feb. 8, 2019.

(51) Int. Cl.
*A61N 1/36* (2006.01)

(52) U.S. Cl.
CPC ..... *A61N 1/36071* (2013.01); *A61N 1/36062* (2017.08); *A61N 1/36178* (2013.01)

(58) Field of Classification Search
CPC ............ A61N 1/36071; A61N 1/36178; A61N 1/36062; A61N 1/37247; A61N 1/36185
See application file for complete search history.

(56) References Cited

U.S. PATENT DOCUMENTS

| | | |
|---|---|---|
| 5,895,416 A | 4/1999 | Barreras, Sr. et al. |
| 6,181,969 B1 | 1/2001 | Gord |
| 6,516,227 B1 | 2/2003 | Meadows et al. |
| 8,255,060 B2 | 8/2012 | Goetz et al. |
| 8,515,546 B2 | 8/2013 | Goddard et al. |
| 8,606,362 B2 | 12/2013 | He et al. |
| 8,620,436 B2 | 12/2013 | Parramon et al. |
| 9,259,574 B2 | 2/2016 | Aghassian et al. |
| 9,656,081 B2 | 5/2017 | Feldman et al. |
| 9,993,649 B2 | 6/2018 | Astrom et al. |
| 10,576,282 B2 | 3/2020 | Doan et al. |
| 10,874,859 B2 | 12/2020 | Zhang et al. |

(Continued)

*Primary Examiner* — Paula J Stice
(74) *Attorney, Agent, or Firm* — Lewis & Reese, PLLC

(57) ABSTRACT

Software for providing a Graphical User Interface (GUI) for use in a clinician programmer for programming an implantable pulse generator (IPG) or external trial stimulator (ETS) is disclosed. A user may define in the GUI multiple pole configurations (e.g., monopoles, bipoles, etc.) which may be used independently to provide stimulation to a patient via the IPG or ETS's electrode array. Selected of the pole configurations can be linked or associated as a group in the GUI and used to concurrently provide stimulation. The pole configuration group may be steered or moved in the electrode array using a single movement instruction which moves all pole configurations in the group simultaneously. This allows the relative positions of the pole configurations in the group to remain constant as the group is moved.

20 Claims, 15 Drawing Sheets

(56) References Cited

U.S. PATENT DOCUMENTS

| | | |
|---|---|---|
| 2015/0080982 A1 | 3/2015 | Funderburk |
| 2015/0231402 A1 | 8/2015 | Aghassian |
| 2015/0360038 A1 | 12/2015 | Zottola et al. |
| 2016/0144183 A1 | 5/2016 | Marnfeldt |
| 2016/0367822 A1 | 12/2016 | Parramon |
| 2018/0071513 A1 | 3/2018 | Weiss et al. |
| 2018/0071520 A1 | 3/2018 | Weerakoon et al. |
| 2018/0071527 A1 | 3/2018 | Feldman et al. |
| 2018/0140831 A1 | 5/2018 | Feldman et al. |
| 2019/0046800 A1 | 2/2019 | Doan et al. |
| 2019/0083796 A1 | 3/2019 | Weerakoon et al. |
| 2019/0175915 A1 | 6/2019 | Brill et al. |
| 2019/0366104 A1 | 12/2019 | Doan et al. |
| 2020/0230410 A1 | 7/2020 | Zhang et al. |

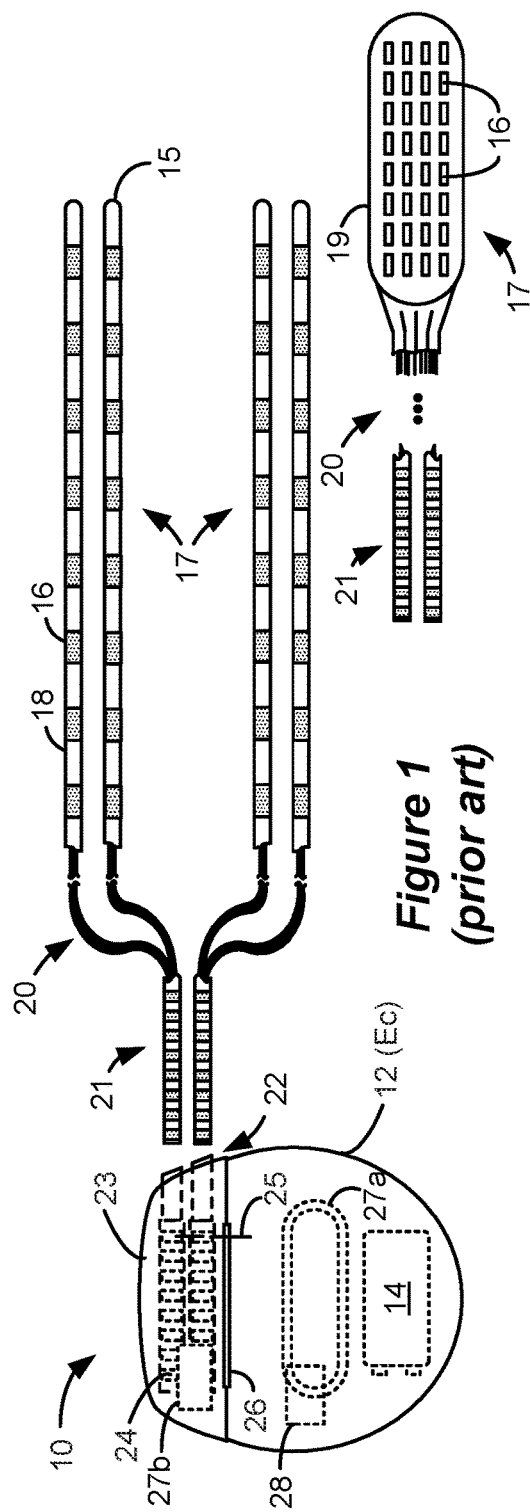
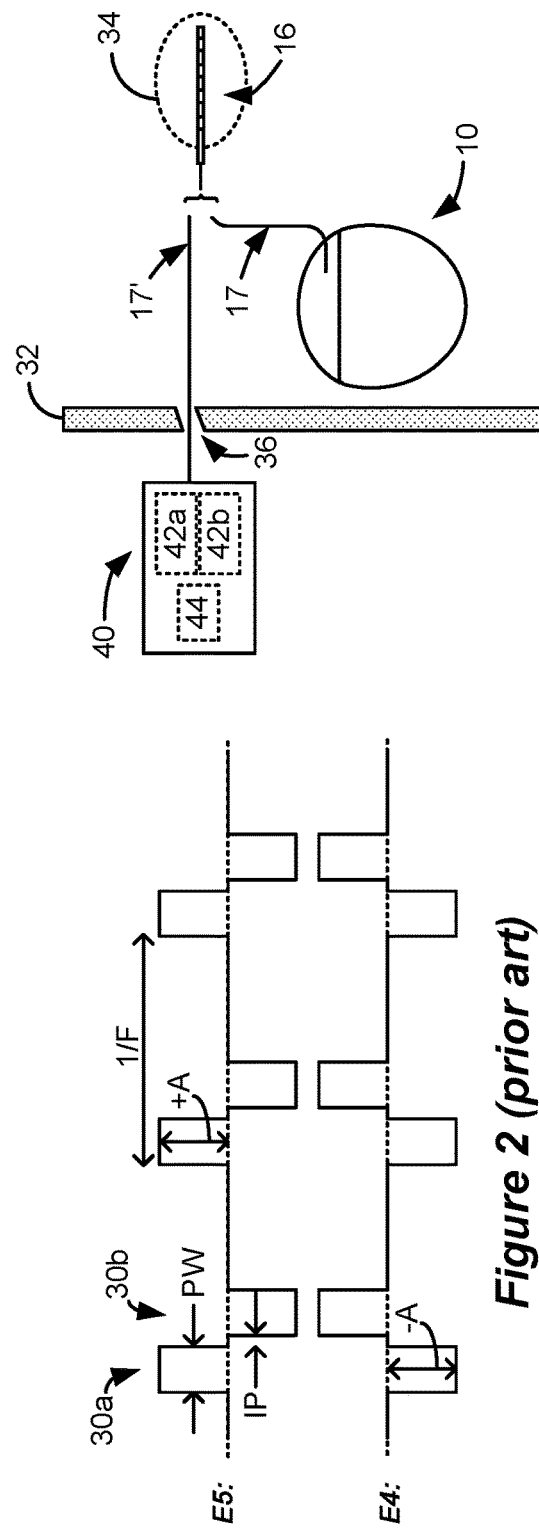
*Figure 1 (prior art)*
*Figure 2 (prior art)*
*Figure 3 (prior art)*

LINKING AND CONCURRENT STEERING OF MULTIPLE POLE CONFIGURATIONS IN A SPINAL CORD STIMULATION SYSTEM

CROSS REFERENCE TO RELATED APPLICATIONS

This is a continuation of U.S. patent application Ser. No. 17/649,767, filed Feb. 2, 2022 (now U.S. Pat. No. 11,850,426), which is a continuation of U.S. patent application Ser. No. 16/774,720, filed Jan. 28, 2020 (now U.S. Pat. No. 11,273,309), which is a non-provisional application of U.S. Provisional Patent Application Ser. No. 62/802,982, filed Feb. 8, 2019. Priority is claimed to these applications, and they are incorporated herein by reference in their entireties.

FIELD OF THE INVENTION

This application relates to Implantable Medical Devices (IMDs), generally, Spinal Cord Stimulators, more specifically, and to methods of control of such devices.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a typically conductive biocompatible device case 12 that holds the IPG's circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura and a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices used to program or monitor the IPG, such as a hand-held patient controller or a clinician's programmer described later with respect to FIG. 5. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like.

Stimulation in IPG 10 is typically provided by pulses, as shown in FIG. 2. Stimulation parameters typically include the amplitude of the pulses (A; whether current or voltage); the frequency (F) and pulse width (PW) of the pulses; the electrodes 16 (E) activated to provide such stimulation; and the polarity (P) of such active electrodes, i.e., whether active electrodes are to act as anodes (that source current to the tissue) or cathodes (that sink current from the tissue). These and other stimulation parameters taken together comprise a stimulation program that the IPG 10 can execute to provide therapeutic stimulation to a patient.

In the example of FIG. 2, electrode E5 has been selected as an anode, and thus provides pulses which source a positive current of amplitude +A to the tissue. Electrode E4 has been selected as a cathode, and thus provides pulses which sink a corresponding negative current of amplitude −A from the tissue. However, more than one electrode may act as an anode at a given time, and more than one electrode may act as a cathode at a given time (e.g., tripole stimulation, quadripole stimulation, etc.).

The pulses as shown in FIG. 2 are biphasic, comprising a first phase 30a, followed quickly thereafter by a second phase 30b of opposite polarity. As is known, use of a biphasic pulse is useful in charge recovery. For example, each electrodes' current path to the tissue may include a serially-connected DC-blocking capacitor, see, e.g., U.S. Patent Application Publication 2016/0144183, which will store charge during the first phase 30a and be discharged (be recovered) during the second phase 30b. In the example shown, the first and second phases 30a and 30b have the same duration and amplitude (although opposite polarities), which ensures the same amount of charge during both phases. This is an example of active charge recovery because the second phase 30b is actively driven by the stimulation circuitry. The second phase 30b may also be charged balance with the first phase 30a if the integral of the amplitude and durations of the two phases are equal in magnitude, as is well known. The width of each pulse, PW, is defined here as the duration of first pulse phase 30a, although pulse width could also refer to the total duration of the first and second pulse phases 30a and 30b as well. Note that an interphase period (IP) during which no stimulation is provided may be provided between the two phases 30a and 30b. Although not shown in FIG. 2, passive charge recovery can also be used to recover charge stored charge, such as is discussed in U.S. Pat. Nos. 10,716,937 and 10,792,491.

IPG 10 includes stimulation circuitry 28 that can be programmed to produce the stimulation pulses at the electrodes as defined by the stimulation program. Stimulation circuitry 28 can for example comprise the circuitry described in U.S. Pat. Nos. 6,181,969, 8,606,362, 8,620,436, 11,040,192, and 10,912,942.

FIG. 3 shows an external trial stimulation environment that may precede implantation of an IPG 10 in a patient. During external trial stimulation, stimulation can be tried on a prospective implant patient without going so far as to implant the IPG 10. Instead, a trial electrode array 17' comprising one or more leads is implanted in the patient's tissue 32 at a target location 34, such as within the spinal column as explained earlier. The proximal ends of the trial lead(s) exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, the trial electrode array 17' is explanted, and a full IPG 10 and its electrode array 17 is implanted as described above; if unsuccessful, the trial array 17' is simply explanted.

Like the IPG 10, the ETS 40 can include one or more antennas to enable bi-directional communications with external devices, explained further with respect to FIG. 4. Such antennas can include a near-field magnetic-induction coil antenna 42a, and/or a far-field RF antenna 42b, as described earlier. ETS 40 may also include stimulation circuitry 44 able to form the stimulation pulses in accordance with a stimulation program, which circuitry may be similar to or comprise the same stimulation circuitry 28 present in the IPG 10. ETS 40 may also include a battery (not shown) for operational power.

FIG. 4 shows various external devices that can wirelessly communicate data with the IPG 10 and the ETS 40, including a patient, hand-held external controller 45, and a clinician programmer 50. Both of devices 45 and 50 can be used to wirelessly send a stimulation program to the IPG 10 or ETS 40—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Pat. No. 9,707,402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna 47a capable of wirelessly communicating with the coil antenna 27a or 42a in the IPG 10 or ETS 40. The external controller 45 can also have a far-field RF antenna 47b capable of wirelessly communicating with the RF antenna 27b or 42b in the IPG 10 or ETS 40.

The external controller 45 can also have control circuitry 48 such as a microprocessor, microcomputer, an FPGA, other digital logic structures, etc., which is capable of executing instructions in an electronic device. Control circuitry 48 can for example receive patient adjustments to stimulation parameters, and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna 27a or 42a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40. If the IPG 10 or ETS 40 includes an RF antenna 27b or 42b, the wand 54, the computing device 51, or both, can likewise include an RF antenna 56b to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by controller circuitry 70 such as a microprocessor, microcomputer, an FPGA, other digital logic structures, etc., which is capable of executing programs in a computing device. In one example, controller circuitry 70 can include any of the i5 Core Processors, manufactured by Intel Corp. Such controller circuitry 70, in addition to executing the clinician programmer software 66 and rendering the GUI 64, can also enable communications via antennas 56a or 56b to communicate stimulation parameters chosen through the GUI 64 to the patient's IPG 10.

A portion of the GUI 64 is shown in one example in FIG. 5. One skilled in the art will understand that the particulars of the GUI 64 will depend on where clinician programmer software 66 is in its execution, which will depend on the GUI selections the clinician has made. FIG. 5 shows the GUI 64 at a point allowing for the setting of stimulation parameters for the patient and for their storage as a stimulation program. Shown to the right is a stimulation parameters interface in which specific stimulation parameters (A, D, F, E, P) can be defined for a stimulation program. Values for stimulation parameters relating to the shape of the waveform (A; in this example, current), pulse width (PW), and frequency (F) are shown in a waveform parameter interface 84, including buttons the clinician can use to increase or decrease these values. Stimulation parameters relating to the electrodes 16 (the electrodes E activated and their polarities P), are made adjustable in an electrode parameter interface 86. Electrode stimulation parameters are also visible and can be manipulated in a leads interface 92 that displays the electrode array 17 or 17' (e.g., its leads) in generally proper position with respect to each other in the patient. Only two percutaneous leads are shown for simplicity. A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current for the selected electrode to be specified in terms of a percentage, X. This is particularly useful if more than one electrode is to act as an anode or cathode at a given time, as explained in the '038 Publication. In accordance with the example waveforms shown in FIG. 2, as shown in the leads interface 92, electrode E5 has been selected (during first phase 30a) as the only anode to source current, and this electrode receives X=100% of the specified anodic current, +A. Likewise, electrode E4 has been selected as the only cathode to sink current, and this electrode receives X=100% of that cathodic current, −A.

While GUI 64 is shown as operating in the clinician programmer 50, the user interface of the external controller 45 may provide similar functionality as the external controller 45 may have similar controller circuitry, software, etc.

SUMMARY

In one example, a system is disclosed, which may comprise: a stimulator device comprising a plurality of electrodes forming an electrode array; and an external device including a non-transitory computer readable medium including instructions that, when executed, are configured to cause the external device to: render a Graphical User Interface (GUI) on the external device, allow a user to specify in the GUI a plurality of pole configurations, wherein each pole configuration is locatable at a position relative to the electrode array, allow the user to link two or more of the pole configurations into a group using the GUI thereby enabling the external device to cause the stimulator device to apply stimulation from each pole configuration in the group concurrently in the electrode array, and allow the user via the GUI to create a single movement instruction configured to simultaneously move the positions of the pole configurations in the group in the electrode array.

In one example, the instructions, when executed, are configured to provide one or more inputs to the GUI, wherein each of the one or more inputs is individually selectable by a user to create the single movement instruction. In one example, the instructions, when executed, are configured to provide a plurality of inputs to the GUI, wherein a user may select a plurality of the inputs to create the single movement instruction. In one example, each pole configuration comprises at least one anode pole and at least one cathode pole capable of forming an electric field in the patient's tissue. In one example, in at least some of the pole configurations, the at least one anode pole, the at least one cathode pole, or both, are located at physical positions of the electrodes in the electrode array. In one example, in at least some of the pole configurations, the at least one anode pole, the at least one cathode pole, or both, are not located at physical positions of the electrodes in the electrode array. In one example, in at least some of the pole configurations, the at least one anode pole and the at least one cathode pole are formed in the electrode array. In one example, the stimulator device comprises a conductive case, wherein at least some of the pole configurations comprise a single anode pole or a single cathode pole formed in the electrode array, and wherein in those at least some pole configurations the conductive case comprises the other of the anode pole or the cathode pole. In one example, the instructions, when executed, are further configured to cause the external device to: allow a user to define in the GUI relative positions of the two or more pole configurations with respect to each other, wherein the single movement instruction is configured to simultaneously move the positions of the linked two or more pole configurations in a manner that preserves their relative positions. In one example, the single movement instruction is configured to simultaneously move the positions of the linked two or more pole configurations in the same direction and the same distance in the electrode array. In one example, the single movement instruction is configured to simultaneously move the positions of the linked two or more pole configurations rotationally in the electrode array. In one example, each pole configuration provides stimulation in the electrode array as a sequence of pulses. In one example, the instructions, when executed, are further configured to cause the external device to cause the stimulator device to apply the stimulation from each pole configuration in the group concurrently such that the pulses of the pole configurations in the group do not completely overlap each other in time. In one example, the instructions, when executed, are further configured to cause the external device to cause the stimulator device to apply the stimulation from each pole configuration in the group concurrently such that the pulses of the pole configurations in the group do not overlap each other at any time. In one example, the stimulator device comprises timing channel circuitry configured to support a plurality of timing channels, wherein the instructions, when executed, are further configured to place the stimulation from each pole configuration in the group into its own one of the timing channels. In one example, the pole configurations in the group physically overlap in the electrode array. In one example, the non-transitory computer readable medium further comprises a library, wherein the library is configured to store the pole configurations, wherein the instructions, when executed, are configured to allow the user to specify the plurality of pole configurations by loading at least one of the plurality of pole configurations from the library using the GUI. In one example, the non-transitory computer readable medium further comprises a library, wherein the instructions, when executed, are further configured to allow the user to store the group of pole configurations.

In one example, a system is disclosed, which may comprise: a stimulator device comprising a plurality of electrodes forming an electrode array; and an external device including a non-transitory computer readable medium including instructions that, when executed, are configured to cause the external device to: render a Graphical User Interface (GUI) on the external device, allow a user to specify in the GUI a group comprising a plurality of pole configurations thereby enabling the external device to cause the stimulator device to apply the stimulation from each pole configuration in the group concurrently in the electrode array, wherein relative positions of the plurality of pole configurations in the group are defined with respect to each other, and allow the user via the GUI to create a single movement instruction configured to simultaneously move the positions of the pole configurations in the group in the electrode array in a manner that preserves their relative positions.

In one example, the instructions, when executed, are configured to provide one or more inputs to the GUI, wherein each input is individually selectable by a user to create the single movement instruction. In one example, the instructions, when executed, are configured to provide a plurality of inputs to the GUI, wherein a user may select a plurality of the inputs to create the single movement instruction. In one example, each pole configuration comprises at least one anode pole and at least one cathode pole capable of forming an electric field in the patient's tissue. In one example, in at least some of the pole configurations, the at least one anode pole, the at least one cathode pole, or both, are located at physical positions of the electrodes in the electrode array. In one example, in at least some of the pole configurations, the at least one anode pole, the at least one cathode pole, or both, are not located at physical positions of the electrodes in the electrode array. In one example, in at least some of the pole configurations, the at least one anode pole and the at least one cathode pole are formed in the electrode array. In one example, the stimulator device comprises a conductive case, wherein at least some of the pole configurations comprise a single anode pole or a single cathode pole formed in the electrode array, and wherein in those at least some pole configurations the conductive case comprises the other of the anode pole or the cathode pole. In one example, the single movement instruction is configured to simultaneously move the positions of the pole configurations in the same direction and the same distance in the electrode array. In one example, the single movement instruction is configured to simultaneously move the positions of the pole configurations rotationally in the electrode array. In one example, each pole configuration provides stimulation in the electrode array as a sequence of pulses. In one example, the instructions, when executed, are further configured to cause the external device to cause the stimulator device to apply the stimulation from each pole configuration in the group concurrently such that the pulses of the pole configurations in the group do not completely overlap each other in time. In one example, the instructions, when executed, are further configured to cause the external device to cause the stimulator device to apply the stimulation from each pole configuration in the group concurrently such that the pulses of the pole configurations in the group do not overlap each other at any time. In one example, the stimulator device comprises timing channel circuitry configured to support a plurality of timing channels, wherein the instructions, when executed, are further configured to place the stimulation from each pole configuration in the group into its own one of the timing channels. In one example, the pole configurations in the group physically overlap in the electrode array. In one example, the non-transitory computer readable medium further comprises a library, wherein the library is configured to store groups of pole configurations, wherein the instructions, when executed, are configured to allow the user to specify the group of pole configurations by loading it from the library using the GUI. In one example, the instructions, when executed, are configured to provide one or more inputs to the GUI to allow a user to adjust the defined relative positions of the plurality of pole configurations with respect to each other.

In one example, a system is disclosed, which may comprise: a stimulator device comprising a plurality of electrodes forming an electrode array, wherein the stimulator device comprises timing channel circuitry configured to support a plurality of timing channels; and an external device including a non-transitory computer readable medium including instructions that, when executed, are configured to cause the external device to: render a Graphical User Interface (GUI) on the external device, allow a user to specify in the GUI a first pole configuration configured to provide stimulation in a first of the timing channels and at a first position relative to the electrode array, allow a user to specify in the GUI a second pole configuration configured to provide stimulation in a second of the timing channels and at a second position relative to the electrode array, wherein the GUI allows the user to link the first and second pole configurations together as a controllable group, and enable the stimulator device to concurrently apply the stimulation from the first and second pole configurations at the respective first and second positions in the electrode array using the first and second timing channels.

In one example, the instructions, when executed, are configured to allow the user via the GUI to create a single movement instruction configured to simultaneously move the first and second positions of the first and second pole configurations in the group in the electrode array. In one example, the instructions, when executed, are configured to provide one or more inputs to the GUI, wherein each of the one or more inputs is individually selectable by a user to create the single movement instruction. In one example, the instructions, when executed, are configured to provide a plurality of inputs to the GUI, wherein a user may select a plurality of the inputs to create the single movement instruction. In one example, the single movement instruction is configured to simultaneously move the positions of the linked two or more pole configurations in the same direction and the same distance in the electrode array. In one example, the single movement instruction is configured to simultaneously move the positions of the linked two or more pole configurations rotationally in the electrode array. In one example, the instructions, when executed, are configured to provide one or more inputs to the GUI to allow a user to adjust the second position relative to the first position. In one example, each of the first and second pole configurations comprises at least one anode pole and at least one cathode pole capable of forming an electric field in the patient's tissue. In one example, in at least some of the first and second pole configurations, the at least one anode pole, the at least one cathode pole, or both, are located at physical positions of the electrodes in the electrode array. In one example, in at least some of the first and second pole configurations, the at least one anode pole, the at least one cathode pole, or both, are not located at physical positions of the electrodes in the electrode array. In one example, in at least some of the first and second pole configurations, the at least one anode pole and the at least one cathode pole are formed in the electrode array. In one example, the stimulator device comprises a conductive case, wherein at least some of the first and second pole configurations comprise a single anode pole or a single cathode pole formed in the electrode array, and wherein in those at least some pole configurations the conductive case comprises the other of the anode pole or the cathode pole. In one example, each pole configuration provides stimulation in the electrode array as a sequence of pulses. In one example, the instructions, when executed, are further configured to cause the external device to cause the stimulator device to apply the stimulation from the first and second pole configurations concurrently such that the pulses of the pole configurations in the group do not completely overlap each other in time. In one example, the instructions, when executed, are further configured to cause the external device to cause the stimulator device to apply the stimulation from the first and second pole configurations concurrently such that the pulses of the pole configurations in the group do not overlap each other at any time. In one example, the first and second pole configurations physically overlap in the electrode array. In one example, the non-transitory computer readable medium further comprises a library, wherein the library is configured to store the first and second pole configurations, wherein the instructions, when executed, are configured to allow the user to specify the first and second pole configurations by loading them from the library using the GUI. In one example, the non-transitory computer readable medium further comprises a library, wherein the instructions, when executed, are further configured to allow the user to store the group of first and second pole configurations.

BRIEF DESCRIPTION OF THE DRAWINGS

FIG. 1 shows an Implantable Pulse Generator (IPG) useable for Spinal Cord Stimulation (SCS), in accordance with the prior art.

FIG. 2 shows an example of stimulation pulses producible by the IPG, in accordance with the prior art.

FIG. 3 shows use of an External Trial Stimulator (ETS) useable to provide stimulation before implantation of an IPG, in accordance with the prior art.

FIG. 6A shows a GUI for moving or steering a pole configuration, specifically a bipole, within an electrode array during a sweet spot search, while

DETAILED DESCRIPTION

In an SCS application, it is desirable to determine a therapeutic stimulation program that will be effective for each patient. A significant part of determining an effective therapeutic stimulation program is to determine a "sweet spot" for stimulation in each patient, i.e., to select which electrodes in the electrode array 17 or 17' should be active and with what polarities and relative amplitudes (X %) to recruit and thus treat a neural site related to pain processing in a patient. Selecting electrodes proximate to this neural site can be difficult to determine, and experimentation-"sweet spot searching"—is typically undertaken to select the best combination of electrodes to provide a patient's therapy.

Figure 5:
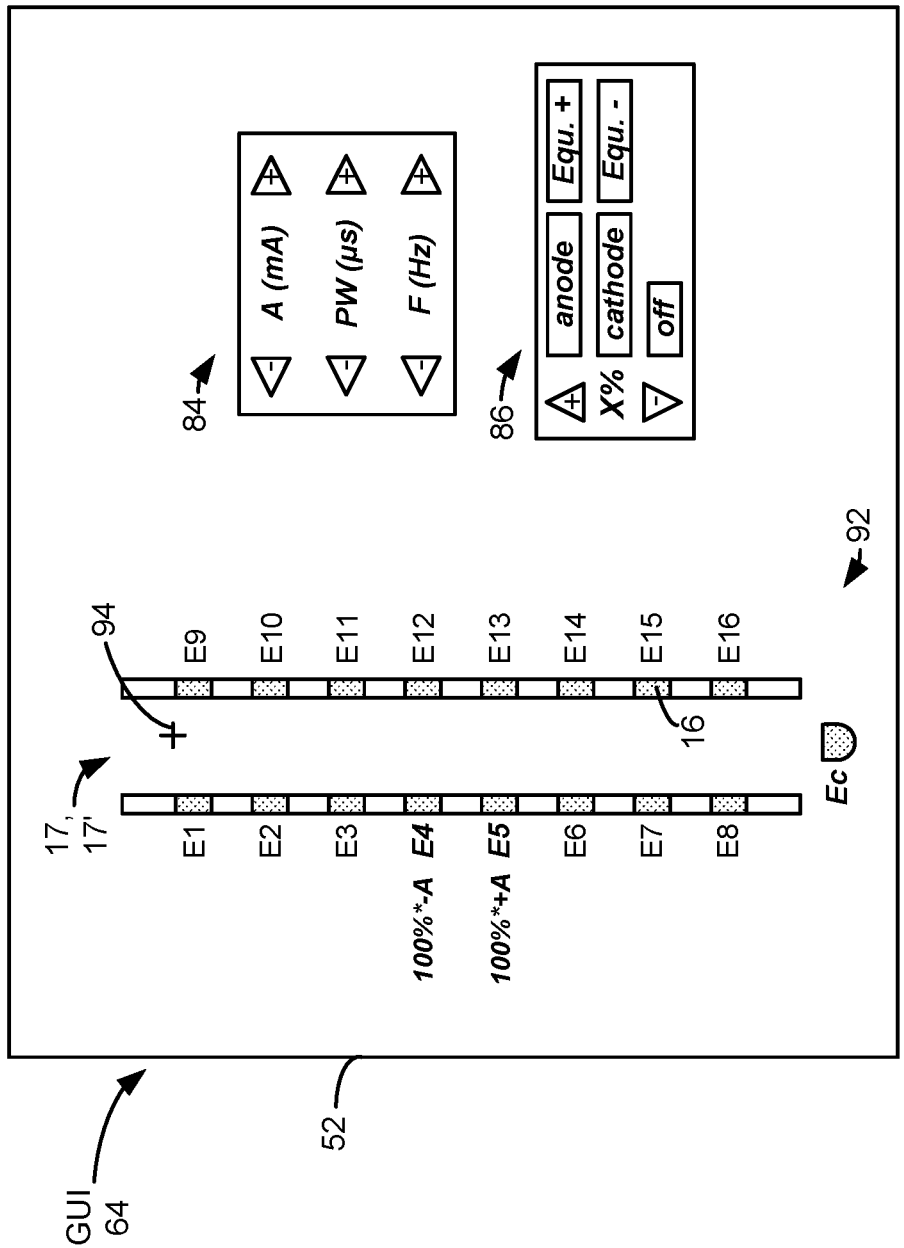
FIG. 5 shows a Graphical User Interface (GUI) of a clinician programmer external device for setting or adjusting stimulation parameters, in accordance with the prior art.
Figure 6A:
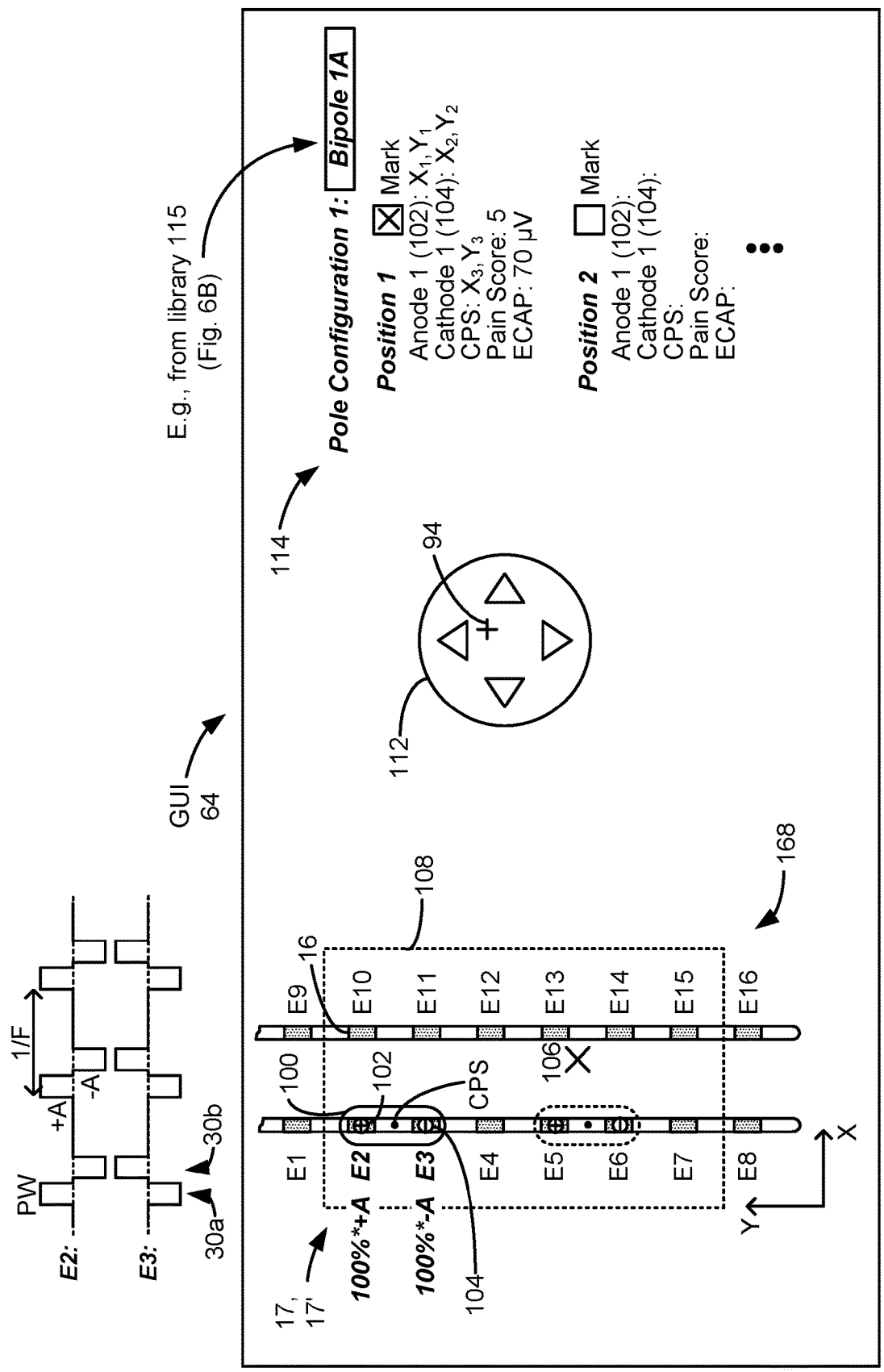

FIG. 6A describes an example sweet spot searching, and shows additional aspects of GUI 64 (FIG. 5) that can be used to define a pole configuration that can be steered through the electrode array 17 or 17' during sweet spot searching. As will be explained further below, a pole configuration comprises at least one anode pole and at least one cathode pole and thus is capable of forming an electric field in the patient's tissue which may stimulate the patient's tissue. Each pole configuration can comprise at least one pole which is formed in the electrode array 17 or 17'; if only one pole is formed in the electrode array 17 or 17', the conductive case electrode Ec 12 can be used as a return to form a pole of the opposite polarity. Otherwise, the at least one anode pole and at least one cathode pole can be formed in the electrode array 17 or 17'. The poles in a pole configuration can appear at the physical position of the electrodes in the array 17 or 17', or can comprise virtual poles formed at arbitrary positions in the array, which can occur by fractionalizing the current at different of the electrodes, again as explained below.

Sweet spot searching is particularly useful after a patient is first implanted with an electrode array, i.e., after receiving their IPG or ETS, although it can also occur at any point during the patient's use of their IPG. Leads over time may migrate in a patient, and therefore sweet spot searching can occur from time to time as necessary to adjust the patient's therapy. In the example shown, it is assumed that a neural target site 106 is likely within a tissue region 108 in which the electrode array is implanted. Such region 108 may be deduced by a clinician based on the patient symptoms, e.g., by understanding which electrodes are proximate to certain vertebrae (not shown), such as within the T9-T10 interspace.

Figure 6B:
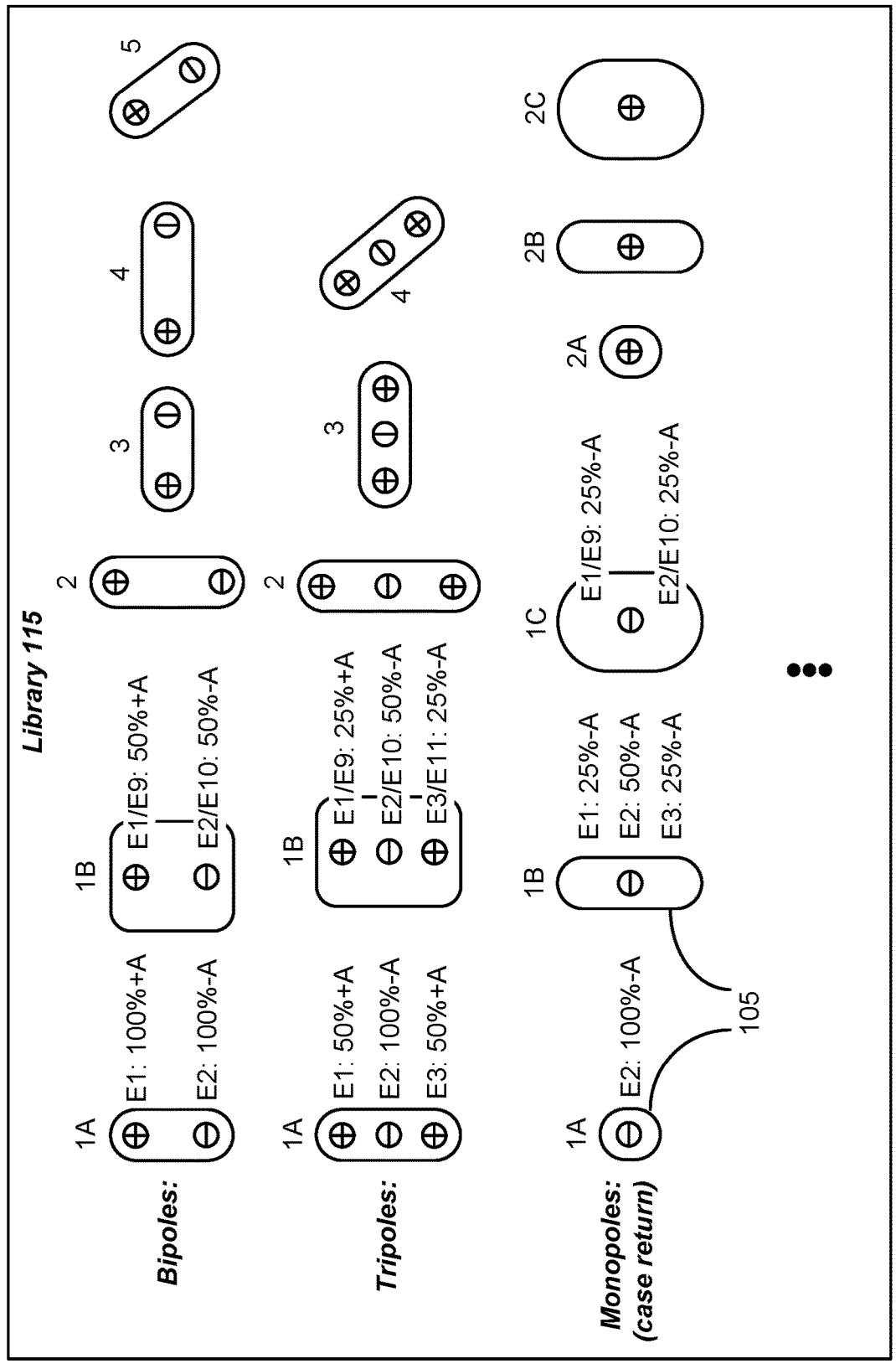
FIG. 6B shows a library of pre-set pole configurations that can be used.

In FIG. 6A, a pole configuration (Pole Configuration 1) is selected or defined using a pole configuration aspect 114 of the GUI 64 to provide stimulation during sweet spot searching. In this example, the pole configuration is a bipole 100 having one anode pole 102 and one cathode pole 104, although other pole configurations having different numbers of anode or cathode poles can also be chosen as described in later examples. Various pre-defined pole configurations can be stored in a library 115 in the clinician programmer 50 as shown in FIG. 6B, and thus aspect 114 may have an option to select or load a pole configuration from the library 115. The configurations in the library 115 may pre-define the relative positions of the poles (whether they are horizontal, vertical, or angled, and the distance between the poles), and the relative amounts of anodic and cathodic current each pole is to receive, which is shown for just some of the example pole configurations in FIG. 6B. The pole configurations may also result in the generation of electric field of different sizes in the patient's tissue, as shown generally by element 105, and as explained further below. Use of a library 115 to pre-define pole configurations is not strictly necessary, and instead a pole configuration may also be manually set or adjusted in the pole configuration aspect 114 or using other aspects of the GUI 64 (FIG. 5) which allow the selection of active electrodes.

In this example of FIG. 6A, the bipole 100 (e.g., Bipole 1A as loaded from the library) is placed in a first position (Position 1), and in this position anode pole 102 is positioned at electrode E2 and so will source a positive current (+A) to the patient's tissue, while cathode pole 104 is placed at electrode E3 and so will sink a negative current (−A) from the tissue. The positions of anode and cathode poles 102 and 104 can also be defined using X-Y coordinates ($X_1$, $Y_1$ and $X_2$, $Y_2$) in the electrode array 17 or 17'. This is particularly useful when the electrodes in the electrode array 17 or 17' span in two dimensions, such as when a plurality of percutaneous leads are used (as shown), or when a paddle lead 19 (FIG. 1) is used. However, positions may be three-dimensional in more complicated examples, or one-dimensional, such as when a single percutaneous lead is used. As shown in the waveforms of FIG. 6A, the stimulation to be used during sweet spot searching is biphasic with first and second phases 30a and 30b, where second phase 30b provides active charge recovery, similar to what was explained earlier with respect to FIG. 2. Passive charge recovery could also be used, but is not shown. In this example, whether poles 102 and 104 are anodes or cathodes is defined with respect to the first phases 30a of the biphasic pulses.

It can be useful to define a single position indicative of the position of the pole configuration, such as a central point of stimulation, or CPS. The CPS can be determined based on the position of the poles 102 and 104, and may comprise a point at which the electric field in the tissue would be strongest. Alternatively, the CPS of a pole configuration may simply be a geometrically central point between the poles or a central point of the electric field. The position of a particular pole configuration can also be defined in other manners in other examples, and need not be defined by a center. In the case of bipole 100, the CPS is logically defined at a position directly between the two poles 102 and 104 as shown in FIG. 6. Thus, in the example shown, the CPS is located at a position $X_3$, $Y_3$ that is between electrodes E2 and E3, as reflected in pole configuration aspect 114. The positions of the poles may also be determined from the position of the CPS. In this regard, pole configuration aspect 114 may include, or have access to (e.g., library 115), other information about the relative position of the poles 102 and 104. For example, poles 102 and 104 may be spaced a certain distance apart in the Y direction (such as at the distance between two consecutive electrodes), which distance may be pre-defined in the library 115. Using such relative positioning information, the positions of the poles 102 and 104 can then be determined from a specified position for the CPS.

The positions of the poles 102 and 104, or the position of the CPS, or both, can be manually entered or adjusted in the pole configuration aspect 114 (or may be provided by the selected pole configuration from the library 115). Alternatively, such positions may be selected using cursor 94. For example, the user can click on a graphic of the electrode array 17 or 17' in leads interface 168 to set the positions of the poles 102 and 104 (from which the CPS position can be determined), or to set the position of the CPS (from which the pole positions can be determined).

Figure 6C:
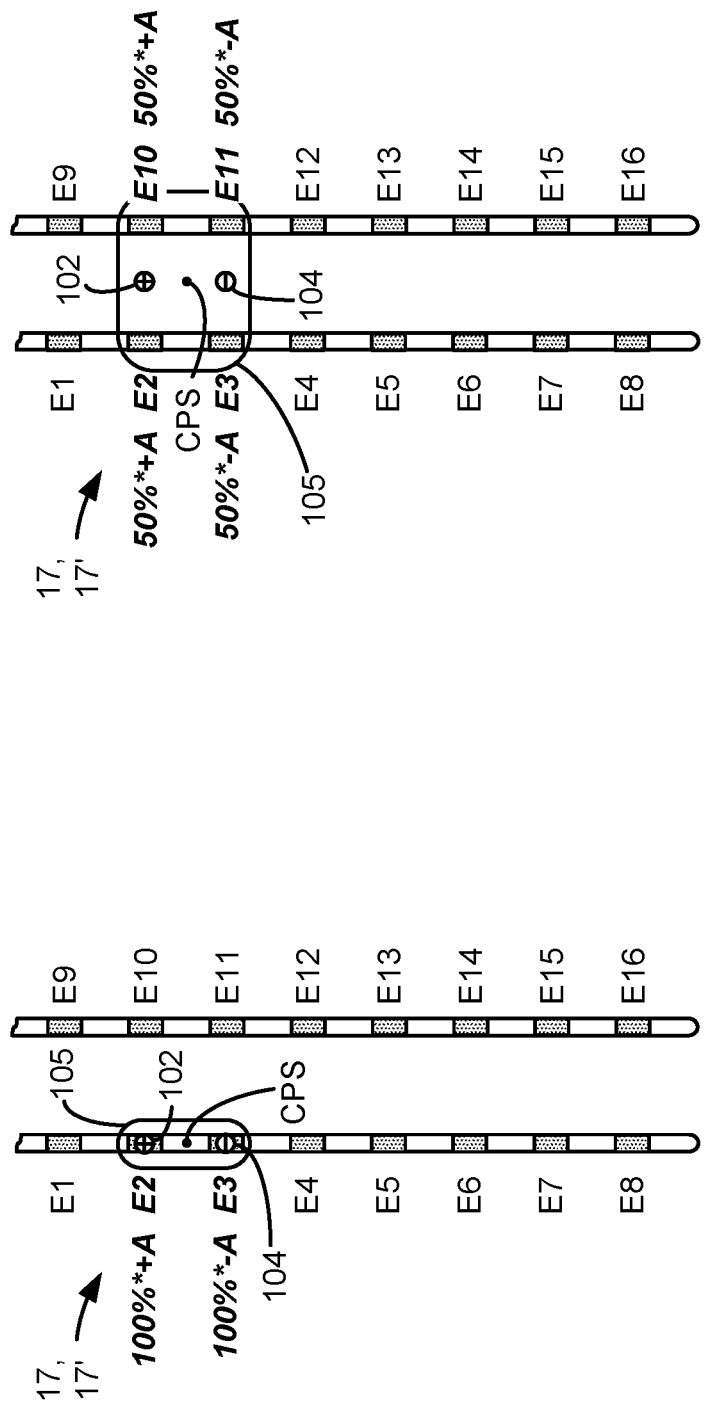
FIG. 6C shows how a pole configuration can be formed with electric fields of a different sizes and shapes.

As mentioned earlier, different pole configurations can affect larger or smaller electric fields in the patient's tissue, as illustrated in FIG. 6C. Creating pole configurations with smaller or larger fields can be affected by activating more or fewer electrodes in the electrode array 17 or 17'. FIG. 6C illustrates two different bipoles again with an anode pole 102 and a cathode pole 104, but affecting different sized electrodes fields 105. Here it is assumed that the bipoles are as pre-defined in library 115 (FIG. 6B), with bipole 1A having a smaller electric field in the horizontal direction, and bipole 1B having a larger electric field in the horizontal direction. Bipole 1A, also used in FIG. 6A, is formed using electrodes (e.g., E2 and E3) that are vertical, thus forming bipole 1A with a relatively small horizontal spread. By contrast, bipole 1B's electric field has a larger horizontal spread, and this is affected by forming this bipole using additional horizontally-spaced electrodes. For example, horizontally-spaced electrodes E2 and E10 are used to form anode pole 102, with each sharing the anodic current +A equally (50%*+A). Likewise, horizontally-spaced electrodes E3 and E11 are used to form cathode pole 104, with each sharing the cathodic current −A equally (50%*−A). The result is that the anode and cathode poles 102 and 104 are between these electrodes, with the CPS between the poles and centered between the two leads in the electrode array 17 or 17'.

Referring again to FIG. 6A, during sweet spot searching, the bipole 100 is provided to the patient at the first position (Position 1) for a short duration, during which the efficacy of the bipole in addressing the patient's symptoms is determined. Such efficacy determination may be subjective based on patient feedback, or objective using measurements taken from the patient. A subjective determination may comprise the patient providing a pain score, which can be entered into aspect 114 and associated with the positions of the poles 102 and 104, and/or the position of the CPS. The pain score can comprise a scale from 1-10 using a Numerical Rating Scale (NRS) or the Visual Analogue Scale (VAS), with 1 denoting no or little pain and 10 denoting a worst pain imaginable. An objective determination can comprise measuring a neural response in the patient. In one example, a neural response can comprise an Evoked Compound Action Potential (ECAP), which may be measured at one or more of the electrodes in the array. In one example, a magnitude of the ECAP (e.g., in μV) can be measured to determine how effectively the stimulation provided by bipole 100 is recruiting neural tissue. Objective and subjective measurements are discussed further in U.S. Patent Application Publication 2020/0230419. The GUI 64 can include an input to mark, and thus store, the efficacy determination in association with relevant position(s).

Figure 4:
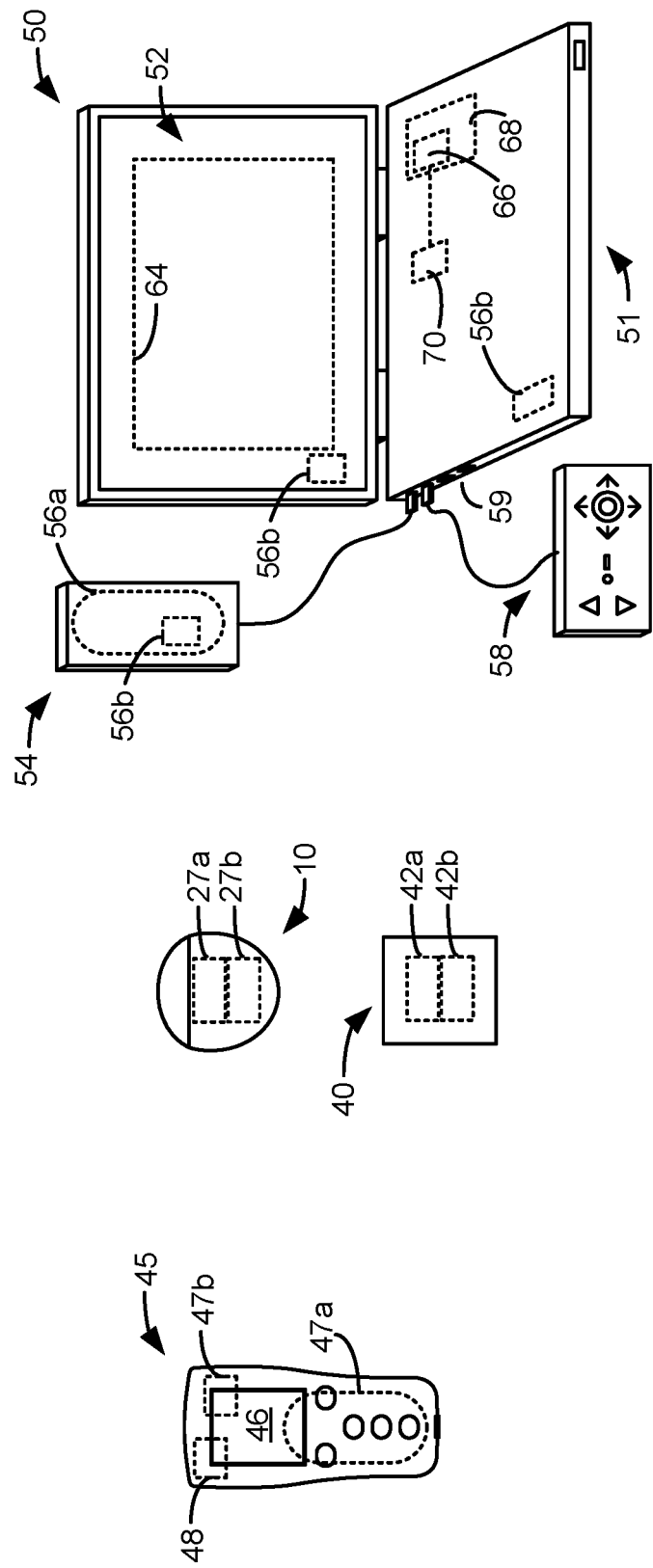
FIG. 4 shows various external devices capable of communicating with and programming stimulation in an IPG and ETS, in accordance with the prior art.

After the bipole 100 is tested at this first position, it can be moved to a different position (Position 2) to test and record its efficacy. Movement of the bipole 100 can occur in different manners. For example, the GUI 64 can include a dial 112 with arrows that allow the clinician to move the bipole 100 up, down, left, and right in the electrode array 17 or 17', which arrows may be engaged using cursor 94. An accessory device associated with the clinician program 50, such as joystick 58 (FIG. 4) can also be used to move the bipole 100. The user may also enter text into the pole configuration aspect 114 to set the bipole's new position as described earlier. As shown in dotted lined in FIG. 6A, the bipole 100 has been moved down the left electrode lead and is currently positioned with poles 102 and 104 at electrodes E5 and E6. (In a real sweet spot searching application, the bipole would probably have been moved in smaller increments to test efficacy at numerous positions in the electrode array 17 or 17'). It is not necessary to move the bipole 100 in any particular path during sweet spot searching, although it may be logical when determining an effective position to move the bipole 100 in a predictable fashion, such as down one lead and up the other. Once several positions of the bipole 100 have been tried and their efficacies recorded, the clinician will now have a better idea of which electrodes are proximate to the target site 106, and are therefore useful to activate for therapeutic stimulation going forward. For example, in FIG. 6A, given the target site 106's proximity to electrodes E13 and E14, it might be expected that therapeutic stimulation involving those electrodes, or electrodes close to them, will provide the best relief for the patient, as reflected for example by the patient's pain scores during the sweet spot search.

Figure 7:
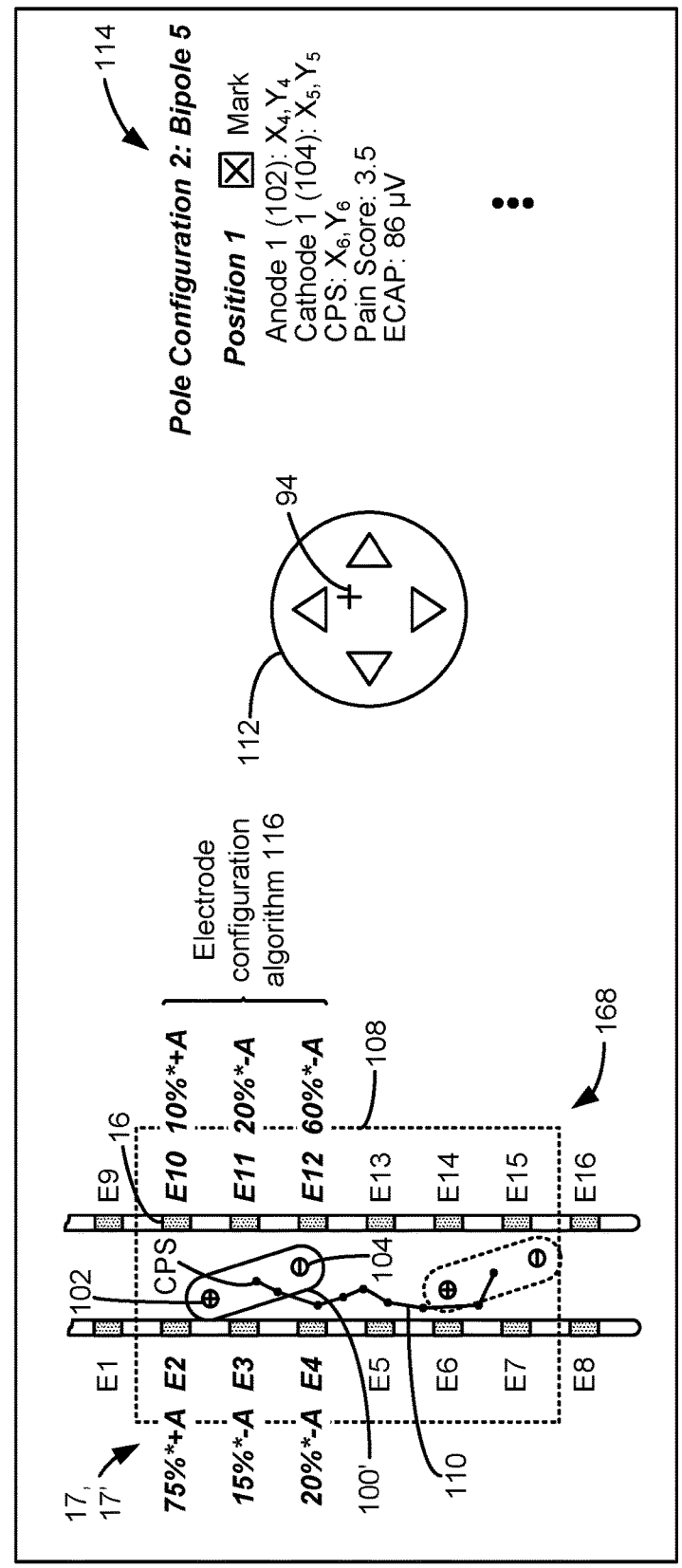
FIG. 7 shows how a pole configuration can be formed with virtual poles that do not necessary correspond with the physical position of electrodes in the electrode array.

A pole configuration need not position the poles 102 and 104 at the exact physical position of the electrodes 16. For example, FIG. 7 shows a bipole 100' where the anode pole 102 and the cathode pole 104 are located at positions ($X_4, Y_4$ and $X_5, Y_5$) that do not coincide with the position of the electrodes. Such poles are often referred to as "virtual" poles. In this example, an electrode configuration algorithm 116 operating as part of the clinician programmer software 66 can be used to compute what physical electrodes should be active, and with what polarities and amplitude fractions (X %), to best form the poles at the prescribed positions. The reader is assumed familiar with electrode configuration algorithm 116, and it is described further for example in U.S. Pat. No. 10,881,859, which is incorporated herein by reference. Thus, the electrode configuration algorithm 116 is only briefly explained.

In the example of FIG. 7, note that the anode pole 102 has been positioned by the user most proximately to electrode E2, but is also generally proximate to electrodes E3 and E10. As a result, the electrode configuration algorithm 116 may designate all of these electrodes as anode electrodes, with them sharing the anodic current +A to different degrees. For example, E2 which is most proximate to anode pole 102 receives the majority of the anodic current (75%*+A), while less proximate electrodes E3 and E10 receive lesser fractions (15%*+A and 10%*+A respectively). Similarly, electrodes E4, E11, and E12, which are generally proximate to the cathode pole 104, may be determined by the electrode configuration algorithm 116 to share appropriate fractions of the cathodic current (20%*−A, 20%*−A, and 60%*−A respectively). Waveforms at these affected electrodes are shown in FIG. 7 to better understand the manner in which the electrode configuration algorithm 116 automatically fractionalizes the anodic and cathodic currents +A and −A to best locate poles 102 and 104 at their prescribed positions. Once the positions of the poles 102 and 104 are determined, the position of the pole configuration—e.g., the CPS—can be determined as well ($X_6, Y_6$), as explained above. Or, as explained above, if the position of the CPS is set by the user, the position of the poles 102 and 104 can be determined, again with the electrode configuration algorithm 116 operating to select electrodes to fix the poles at those positions.

Note that the electrode configuration algorithm 116 can also determine the positions of the anode and cathode poles 102 and 104 given a user's selection of particular active electrodes. In this example, the electrode configuration algorithm 116 essentially works in reverse. For example, if it is assumed that the user has activated electrodes E2-E4 and E10-E12 with the polarities and amplitude fractions shown in FIG. 7, the electrode configuration algorithm 116 can compute that this configuration will place the anode pole 102 at position $X_4, Y_4$, and cathode pole at position $X_5, Y_5$.

Because the anode pole 102 and cathode pole 104—with the assistance of the electrode configuration algorithm 116—can be positioned at arbitrary positions, the pole configuration can be moved in very small increments and to arbitrary positions in and around the electrode array 17 or 17'. (Note that the electrode configuration algorithm 116 can also produce poles in a border region outside of the physical boundary of the electrode array, for example by using anodes to "push" the stimulation beyond the boundary). Such movement is shown by path 110 in FIG. 7, which tracks movement of bipole 100's CPS to a final position (shown in dotted lines). Efficacy can be measured and stored at each of these pole configuration positions, again with the hope that the clinician will be able to locate a position (and hence electrodes) that will be effective at providing therapy for the patient going forward.

Figure 8:
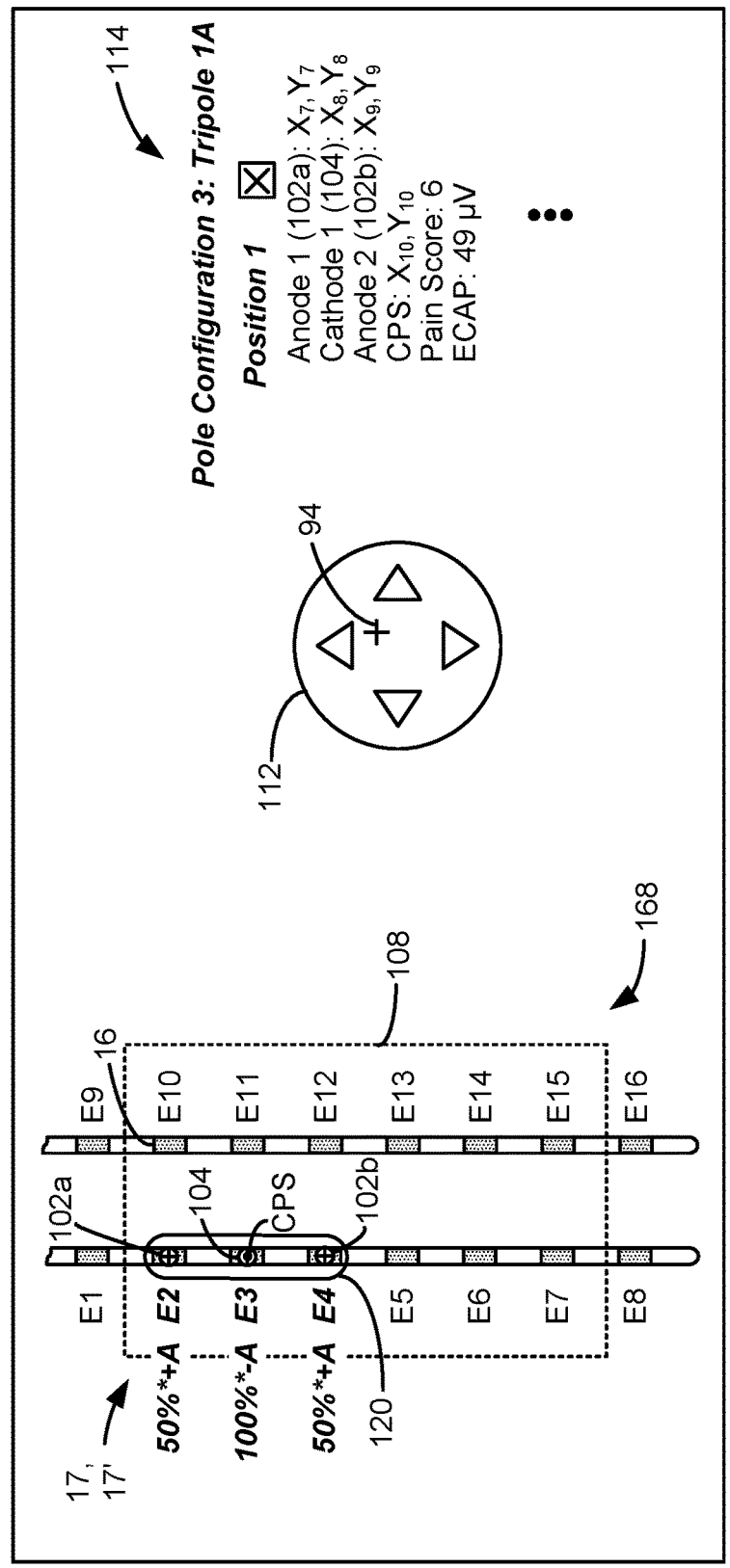
FIG. 8 shows use of a tripole pole configuration during sweet spot searching.

Sweet spot searching can use other types of pole configurations as well, including pole configurations having more than one anode or cathode pole. For example, FIG. 8 shows the example of a tripole 120 having one cathode pole 104 which receives the entirety of the cathodic current −A, and two anode poles 102a and 102b. The anode poles 102a and 102b can share the anodic current +A differently, but in this example they share this current equally (50%*+A). Further, in this example, the anode poles 102a and 102b and the cathode pole 104 are collinear, with the cathode pole 104 between and spaced equidistantly from the anode poles 102a and 102b. However, such linearity and symmetry is not necessary, and the poles 102a, 102b, and 104 can be positioned in any manner with respect to each other. Further, in this example, the anode poles 102a/b and the cathode pole 104 are for simplicity positioned at the physical position of the electrodes 16 (specifically, at electrodes E2, E3, and E4), but as discussed earlier this is not strictly necessary and the poles can with the assistance of electrode configuration algorithm 116 be formed as virtual poles as well. Indeed, poles that initially are positioned at the physical electrodes may be reformulated as virtual poles once the pole configuration is steered to a new position using dial 112 for instance. The CPS in the example of tripole 120 is most logically defined at the position of the central cathode pole 104 (e.g., at E3), but as mentioned earlier the position of a particular pole configuration can defined in other manners. Other pole configuration geometries containing one or more anode or cathode poles are disclosed in U.S. Pat. No. 10,881,859.

Figure 9A:
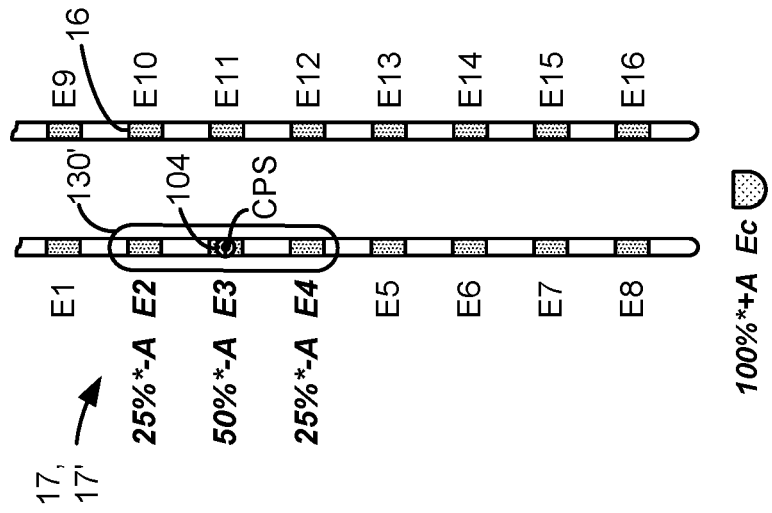
FIGS. 9A and 9B show use of different monopole pole configurations during sweet spot searching.
Figure 9B:
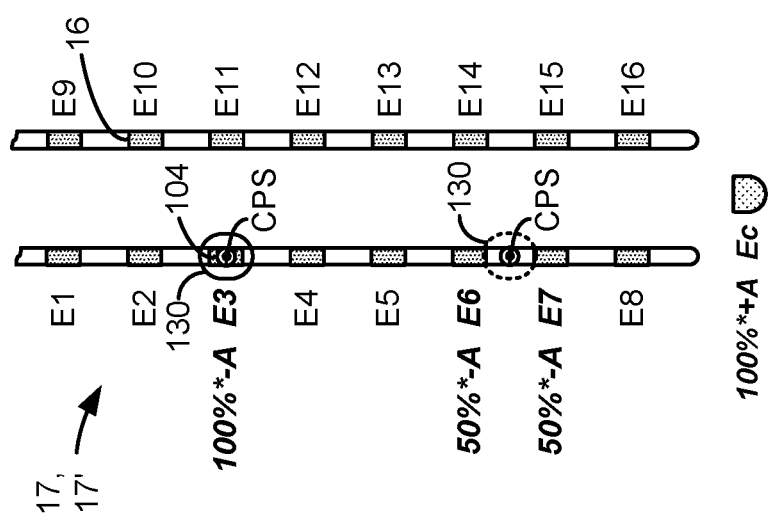

A pole configuration may also comprise only one pole of a particular polarity that is formed in the electrode array 17 or 17'. In this instance, the conductive case electrode Ec 12 (FIG. 1) can comprise a current return, as shown in FIGS. 9A and 9B. In FIG. 9A, a monopole 130—in this example a single cathode pole 104—is initially formed at electrode E3 which receives the entirety of the cathodic current −A. It is therefore sensible to define the CPS of this pole configuration at the position of this singular pole 104 as well. Case electrode Ec provides the entirety of the anodic current A+. FIG. 9A also shows movement of this monopole to a new position, shown in dotted lines. Here, the monopole 130 has been moved to a position such that its CPS is now between electrodes E6 and E7. The electrode configuration algorithm 116 described earlier would thus likely form the monopole 130 at this position by splitting the cathodic current −A equally between electrodes E6 and E7 (50%*−A).

More than one electrode may be activated to form this single cathode pole 104 and to form a larger electric field, as shown in FIG. 9B. In this example, a monopole 130' is formed in which the cathodic current −A is split between three electrodes E2, E3 and E4, with E3 receiving the majority (50%*−A), and E2 and E4 splitting the remainder (25%*−A). Despite the involvement of three electrodes, the CPS of monopole 130' is most logically characterized at E3, or more generally at a point between the active electrodes. If electrodes on the other lead were used to form monopole 130', the electric field could be spread in the horizontal direction, with the CPS appearing between the two leads, although this example isn't shown (see monopole 1C in FIG. 8). It should be understood that the examples of FIGS. 9A and 9B could comprise monopoles having only a single anode pole 102, with the case electrode Ec providing the entirety of the cathodic current −A.

While sweet spot searching as described is generally effective, the inventors see room for improvement. A pain site 106 is generally innervated by many neural fibers which a single pole configuration may be unable to entirely recruit. Thus, the inventors believe that sweet spot searching may be enhanced when multiple pole configuration are used concurrently in a group. Using a group of multiple pole configurations will likely more fully recruit the neural fibers involved in causing patient's symptoms, thus making it easier to locate and cover a pain site 106 during sweet spot searching.

Figure 10:
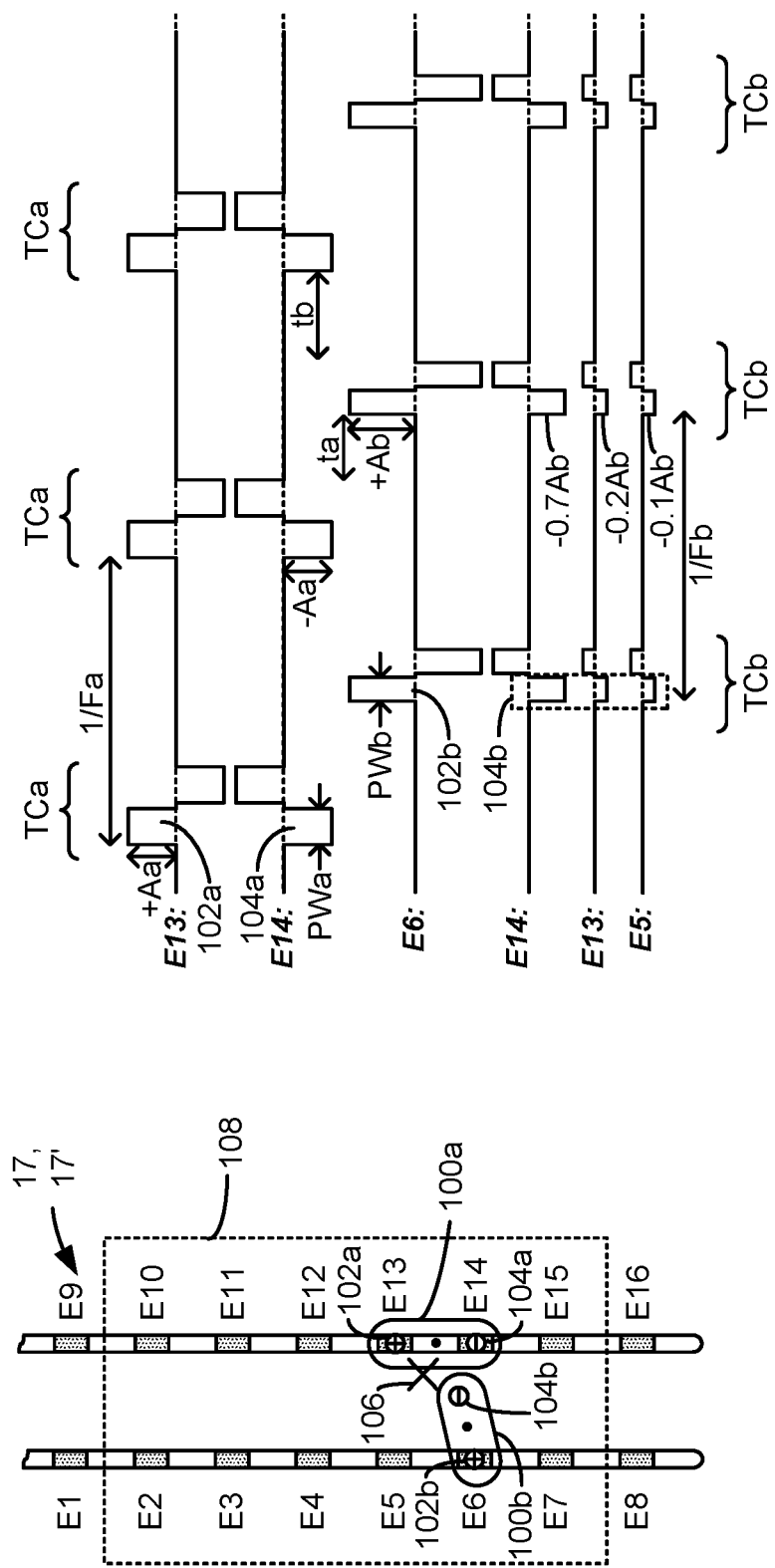
FIG. 10 shows concurrent use of two pole configurations in a group, and shows the waveforms used to form each.

An example of using multiple pole configurations in a group is shown in FIG. 10. In this example, two pole configurations 100a and 100b are used for simplicity, although further numbers of pole configurations could also be used. The pole configurations 100a and 100b are both bipoles in this example, with bipole 100a having an anode pole 102a and a cathode pole 104a, and bipole 100b having an anode pole 102b and a cathode pole 104b. However, any pole configuration could be used, including the tripole and monopole examples illustrated earlier, or other examples.

Each of the bipoles 100a and 100b is formed in accordance with their own stimulation parameters. In this example the waveforms used to form each of the bipoles comprise biphasic pulses with symmetric first and second phases 30a and 30b, similar to what was described earlier with reference to FIG. 2, although waveforms of any shape can be used. The pulses could also comprise bursts of higher frequency pulses, or other random shapes, as is well known. The pulses may also comprise random patterns having pulses of different shapes. Bipole 100a is formed with its own amplitude Aa, pulse width PWa, and frequency Fa. Bipole 100b is formed with its own amplitude Ab, pulse width PWb, and frequency Fb. However, these stimulation parameters may also be equal in the two bipoles 100a and 100b (i.e., Aa=Ab, PWa=PWb, Fa=Fb). Note that the amplitudes Aa and Ab used in each bipole 100a and 100b can be set by the user, and set to sub-perception or supra-perception levels, as described further below. Further, these amplitudes can be set based on objective measures, such as by measuring ECAP amplitudes, as described earlier.

The waveforms show how the bipoles 100a and 100b can be formed when at their current positions. For example, bipole 100a is relatively straight forward, because both poles 102a and 104a happen to coincide with the physical positions of electrode E13 and E14; thus E13 receives the entire anodic current +Aa while E14 receives the total cathodic current −Aa. Bipole 100b's anode pole 102b is located at the physical position of electrode E6, which therefore receives the entire anodic current +Ab. Cathode pole 104b however is virtual and not located at the physical position of an electrode. Therefore, the cathodic current −Ab is split between electrodes in its vicinity, i.e., E5 (10%*−Ab), E13 (20%*−Ab), and E14 (70%*−Ab). Again, the electrode configuration algorithm 116 described earlier can assist in determining what electrodes should be active, and with what polarity and current fractions, to best form the poles at the specified locations for each bipole.

Bipoles 100a and 100b are preferably formed in different timing channels in the IPG or ETS. As is known, timing channels comprise circuitry in the IPG or ETS that can each be programmed with stimulation parameters and operate concurrently to provide stimulation to the patient. Providing stimulation from multiple timing channels concurrently allows more complex stimulation to be provided to the patient's tissue. See, e.g., U.S. Pat. No. 9,656,081 (describing timing channels in an IPG in further detail). A timing channel for each of the pole configurations can be specified in GUI 64 when defining or retrieving these configurations. Note that "concurrent" provision of the pole configurations 100a and 100b means that the pole configurations 100a and 100b are operating at the same time to create their pulses, but does not imply that the pulses in each are concurrent or overlapping in time. In fact, it is preferable that pulses in each of the concurrently-running pole configurations do not perfectly overlap each other at all times (if they did, they together would in effect comprise a singular new pole configuration), and some systems may employ arbitration schemes or logic that prevent pulses from overlapping. Thus, pole configurations can be "concurrently" applied even if their pulses do not overlap or are prevented from overlapping. That being said, it is also permissible if the pulses in the pole configurations overlap in time to some degree (e.g., partially in time). It is also permissible if pulses in the different pole configurations overlap from time to time, such as when the pulses in the different pole configurations are issued at different frequencies, and thus their pulses may occasionally overlap in time.

That being said, the pulses in each pole configuration (timing channel) preferably do not overlap at all with pulses in other pole configurations, as shown in FIG. 10. Therefore, gaps ta appear between the end of the pulses of pole configuration 100a and the beginning of the pulses of pole configuration 100b. Likewise, gaps tb appear between the end of the pulses of pole configuration 100b and the beginning of the pulses of pole configuration 100a. ta and tb can be the same or different, and may be adjustable, as discussed further later. While it is convenient to program concurrently-operating pole configurations in different timing channels, this is not strictly necessary, particularly if the IPG or ETS is capable of making complex waveforms within a single timing channel. See, e.g., U.S. Pat. No. 10,576,265.

Although not shown in this example, note that the pole configurations in a group may overlap in space (i.e., in the electrode array 17 or 17'), even if they do not entirely overlap in time, as explained further below.

Figure 11:
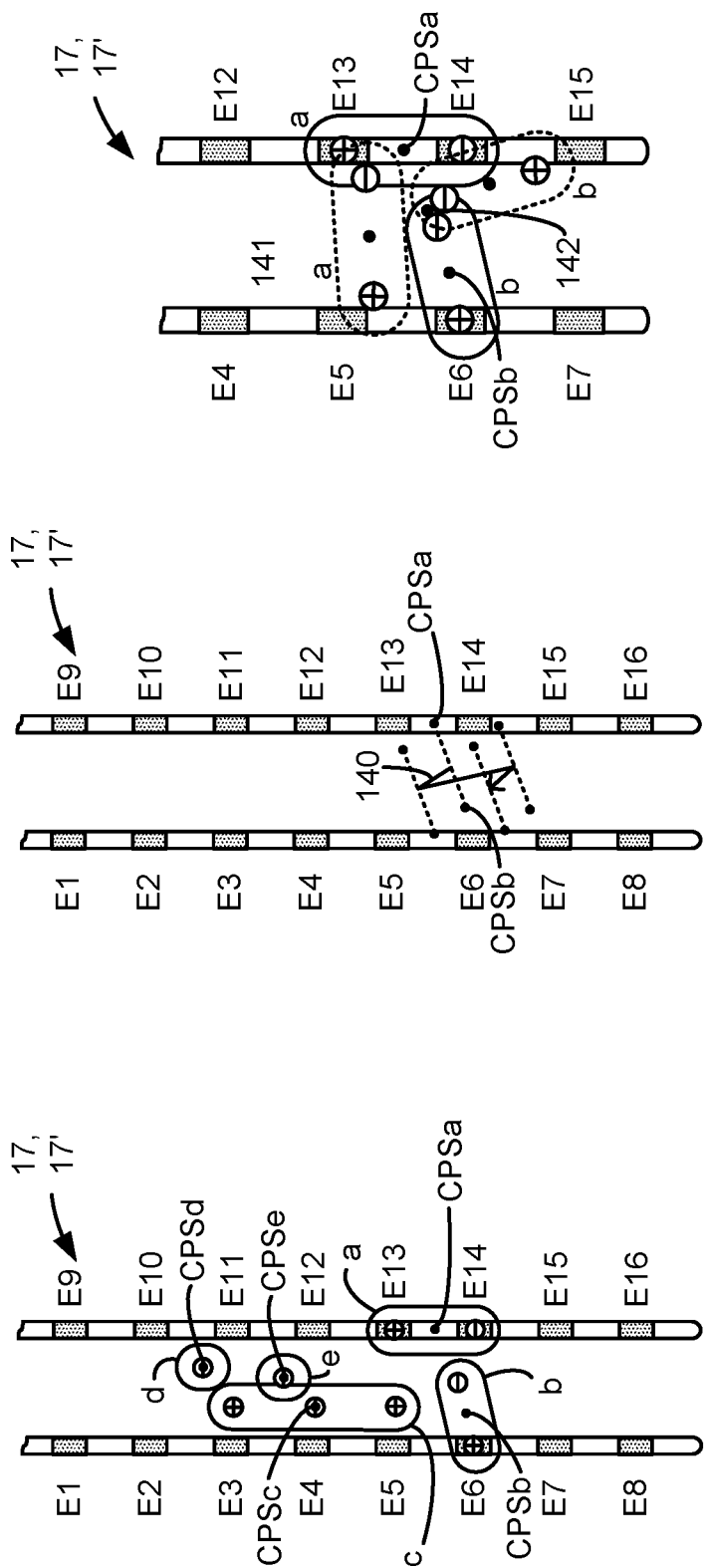
FIGS. 11A-11C show how two or more pole configurations can be linked and steered or rotated together in the electrode array.

If multiple pole configurations are used together as a group during sweet spot searching, it may be beneficial to allow the pole configurations to be steered in unison, and FIG. 11A shows this in a first example. Here, the user has defined, or has retrieved from library 115, five different pole configurations a-e. Pole configurations a and b are bipoles, similar to those described earlier with reference to FIG. 10. Pole configuration c is a tripole, and pole configurations d and e are monopoles having singular cathode poles. The clinician may have been experimenting with all of these pole configurations during sweet spot searching.

Perhaps the clinician notices that pole configurations a and b, when tested individually, seem promising in treating the patient, either based on subjective or objective measurements described earlier. In this case, the relative positions of pole configuration a and b may be significant. As such, it may be desirable to operate them both concurrently (FIG. 10), and to steer them in a manner which keeps their relative positions constant. In other words, it may be desirable to link pole configurations a and b together for steering purposes. This is shown in FIG. 11B. Here the positions of the pole configurations a and b are denoted simply by their CPSs— CPSa and CPSb with the anode and cathode poles removed for simplicity. As can be seen, the two linked pole configurations a and b are simultaneously steered together along a path 140 (i.e., their anode and cathode poles 102 and 104 are moved) such that their positions relative to one another remain constant. In the example of FIG. 11B, this is affected by moving the pole configurations in the same direction and the same distance in the electrode array.

Figure 12:
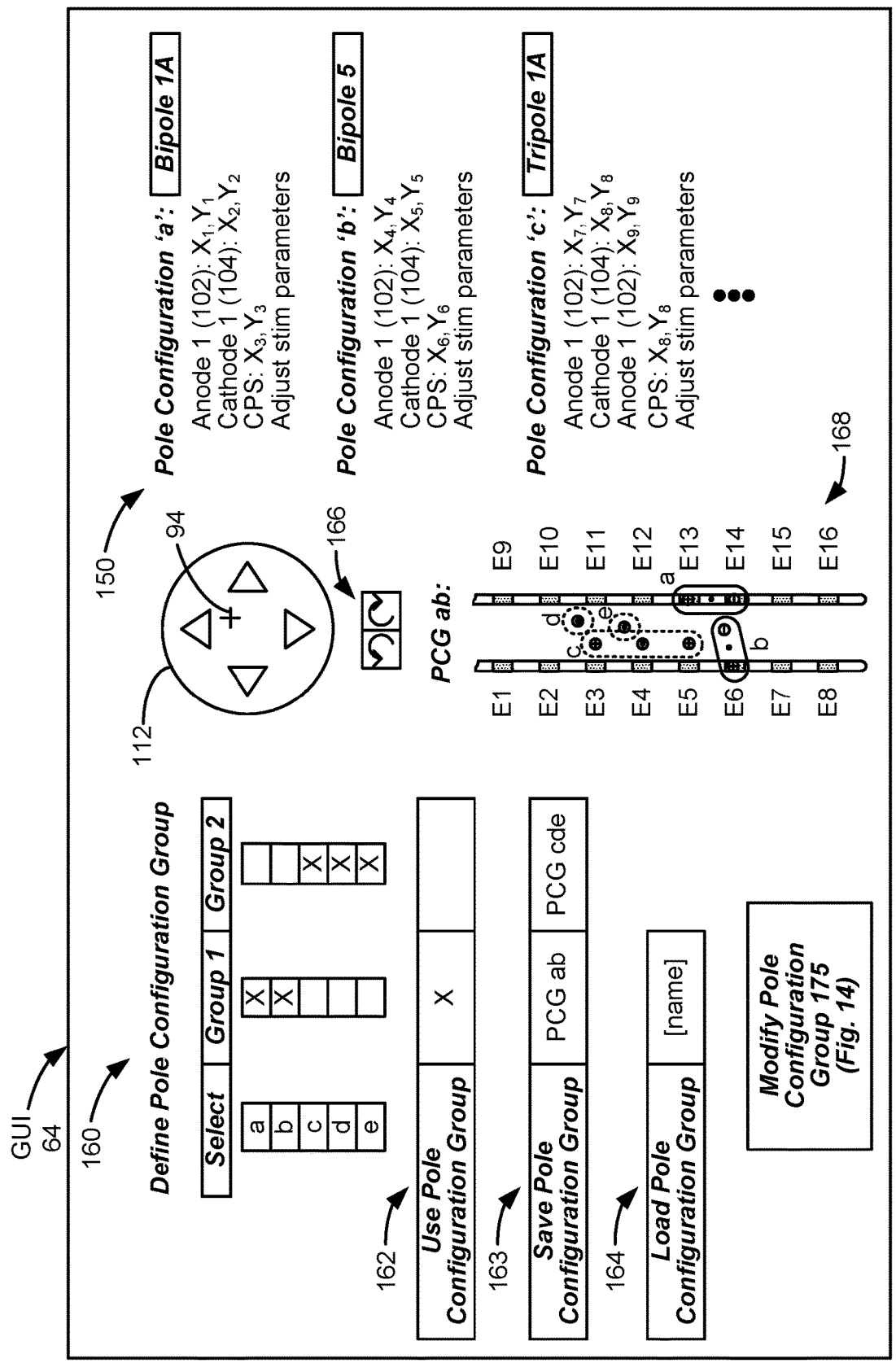
FIG. 12 shows a GUI for defining a multiple pole configuration group, and for steering that group using an electrode array.
Figure 13:
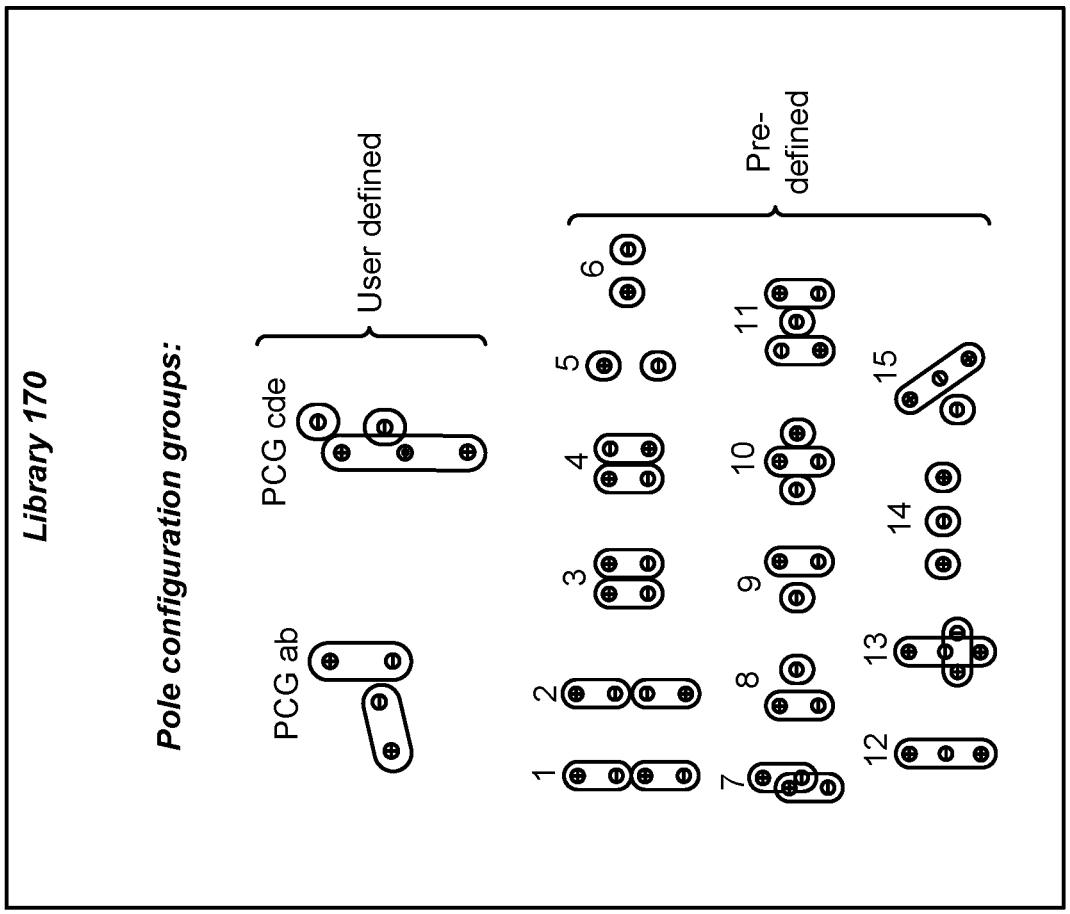
FIG. 13 shows a library of user-defined or pre-defined pole configuration groups.
Figure 14:
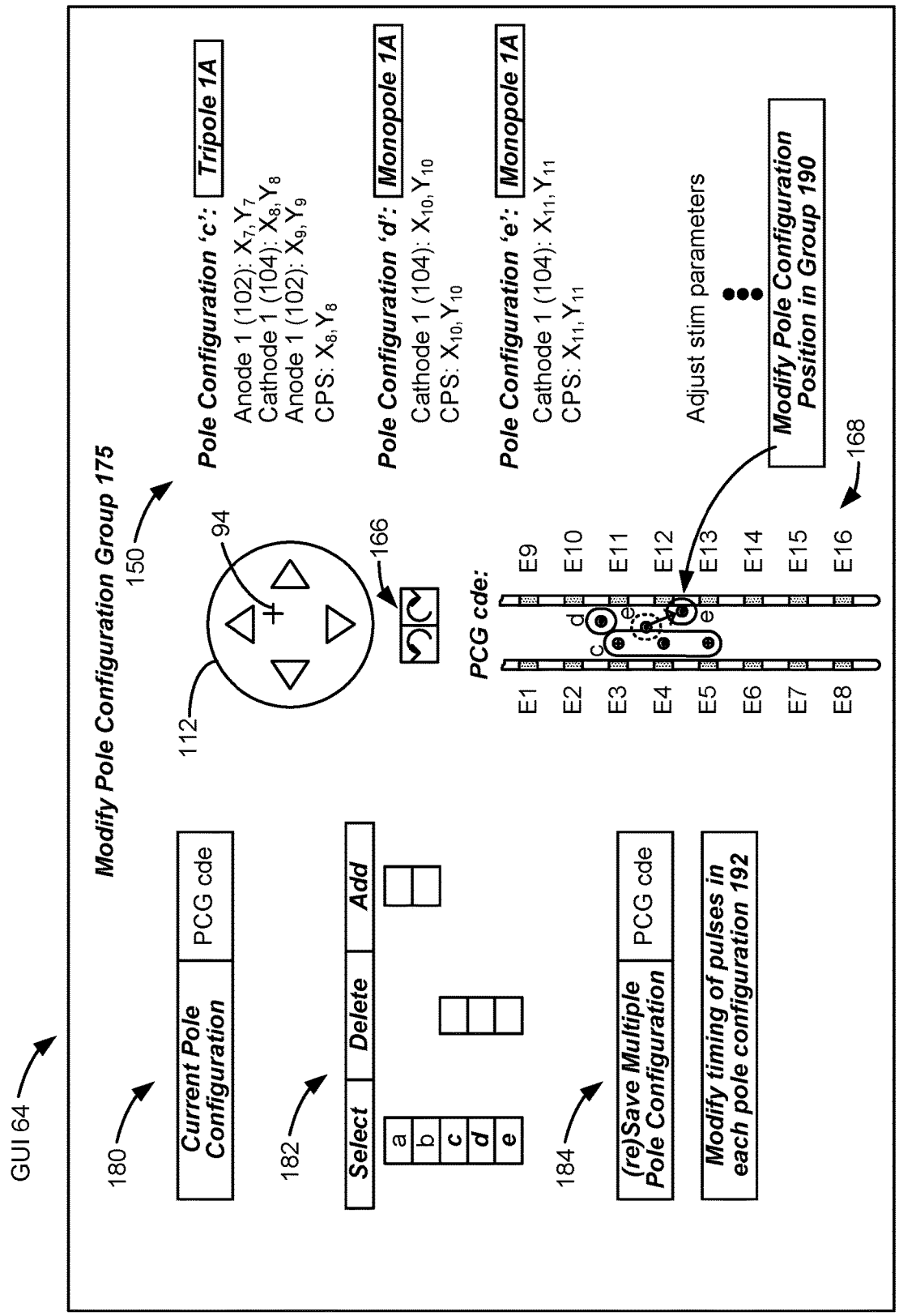
FIG. 14 shows a GUI for modifying a pole configuration group.
Figure 15:
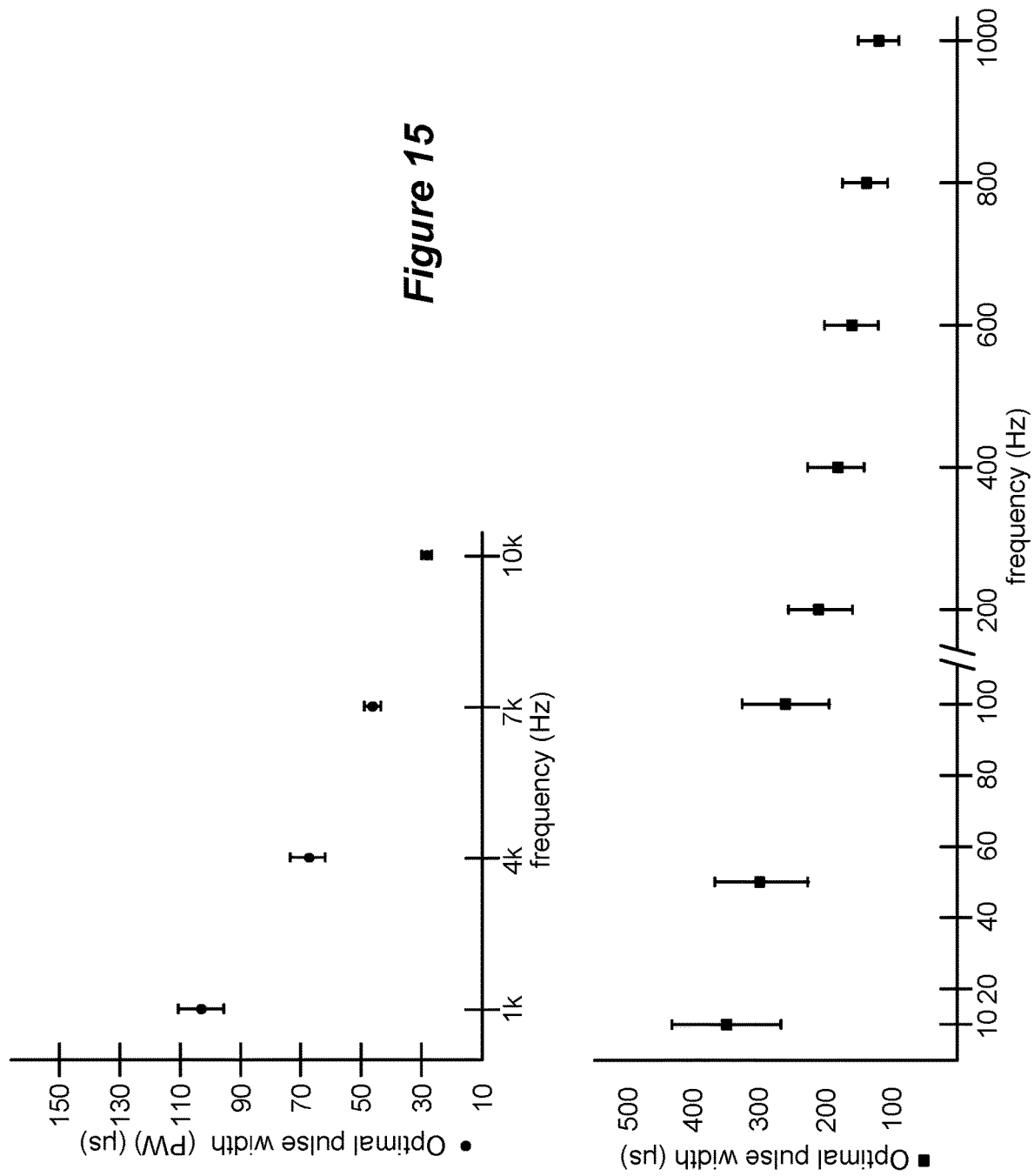
FIG. 15 shows data associating lower frequencies with optimal pulse widths useable to provide sub-perception stimulation in an IPG or ETS.

FIGS. 12-14 shows aspects of the GUI 64 that can be used to link, manage, and steer multiple pole configuration groups. Starting first with FIG. 12, pole configuration aspect 150 shows information for the various independent pole configurations a-e (only a-c are shown for simplicity). Pole configuration aspect 150 can be similar to pole configuration aspects 114 described earlier (FIG. 6A). It can display, of allow adjustment of, the positions of the poles in each pole configuration, as described earlier. Pole configuration aspect 150 may also display, or allow adjustment of, the stimulation parameters used for each pole configuration (e.g., Aa, PWa, Fa, Ab, PWb, Fb, etc.). Adjusting the stimulation parameters for an individual pole configuration in aspect 150 may take the user to a different portion of the GUI 64 where the stimulation parameters can be modified (e.g., FIG. 5). A leads interface 168 can display each of the pole configurations in their current positions in the electrode array 17 or 17'.

Aspect 160 in FIG. 12 allows the various pole configurations a-e to be linked for steering purposes, and in effect allows a multiple pole configuration group to be defined. Each pole configuration a-e can be displayed, along with options to allow the pole configurations to be linked within a group. In the example shown, two pole configurations groups can be defined ("Group 1" and "Group 2"), although one or more groups is also contemplated. As shown, pole configurations a and b have been selected for inclusion in Group 1, while pole configurations c, d, and e have been selected for inclusion in Group 2. Option 162 allows one of the two groups to be selected for use, and currently Group 1 (pole configurations a and b) is being used. Selecting a group for use can update the graphics shown in the leads interface to highlight only the pole configurations in the currently selected group. Thus, as can be seen, pole configurations a and b are drawn in solid lines to denote that this group is currently active. By contrast, unused pole configurations c, d, and e are shown in dotted lines, or may simply not be shown at all in the leads interface 168.

Once a pole configuration group has been selected in this manner, the software 66 in the clinician programmer 50 can operate as necessary to combine the pole configurations in the group and to send the IPG or ETS instructions necessary to form the pulses specified by each pole configuration. For example, and as discussed with reference to FIG. 10, the software 66 may place the individual pole configurations into different timing channels, and otherwise adjust the timing so that the pulses in each will not completely overlap, as discussed earlier. Note that the controller circuitry in the IPG or ETS may also contain arbitration logic that can set the timing of the pulses of each of pole configuration in the group. See, e.g., U.S. Pat. No. 9,656,081 (describing arbitration logic).

Once defined, the pole configuration group may be steered in the electrode array by creating in the clinician programmer a single movement instruction that will move the position of all pole configurations in the group simultaneously and keeping their relative positions constant, as was shown earlier with respect to FIG. 11B. Note that "simultaneous" movement of the pole configurations does not imply that the pole configurations must be moved at exactly the same point in time. For example, the clinician programmer in response to the single movement instruction may create different data packets for the IPG or ETS with each containing the instructions to move each pole configuration, meaning in reality that each may be moved at the IPG or ETS at slightly different times. The difference in these times may be negligible from a therapeutic standpoint. Regardless, even if the pole configurations are technically moved at different times in the IPG or ETS, they are still considered to be moved "simultaneously" if they move in response to the single movement instruction, regardless of how that single movement instruction may be implemented. Further, while it is preferred that the pole configurations are simultaneously moved by the same amount—for example with the pole of each moving the same direction and distance—this is not strictly required. Instead, in other examples, the poles in each pole configurations can simultaneously move in different directions or with different distances in response to the single movement instruction.

A singular movement instruction may be provided by one or more inputs of the GUI, such as by selecting any of the arrows in dial 112, by selecting a new X,Y coordinate for the group, by clicking on a location in the leads interface 168, or by other means described. A single movement instruction may also be created in the clinician programmer in response to a plurality of different inputs to the GUI. Movement of a pole configuration group need not be linear, such as up or down or left and right in the electrode array 17 or 17'. A movement instruction may also move the pole configurations in a group rotationally. Rotation can be provided by option 166 in FIG. 12, which allows a pole configuration group to be rotated clockwise or counterclockwise in the electrode array 17 or 17'. Such rotational movement is shown in FIG. 11C. In this example, the pole configurations in the group have been rotated about 90 degrees counterclockwise around a rotational point 142. Rotation point 142 for the pole configurations in the group can be defined in different ways, such as at a center of their electric fields. However, for simplicity in FIG. 11C, a rotation point 142 between the CPSs of pole configurations a and b (i.e., CPSa and CPSb) has been used. In other options, option 166 can allow the user to define the position of a rotational point 142, such as for example by clicking on a position in the leads interface 168.

Although not shown for simplicity, the GUI 64 may also include options to mark and store various positions of the group, and their measured effectiveness at each position, as explained earlier with the single pole configuration examples of FIG. 6A. Again, such information is useful during sweet spot searching to allow the clinician to understand a position for the pole configuration group that is most effective for the patient.

Once defined, the pole configuration groups can be named (PCG ab, PCG cde) and stored using option 163. A stored pole configuration group may be stored in a library 170 in the clinician programmer 50, as shown in FIG. 13. Library 170 is similar to, and can comprise part of, library 115 used to store information for the individual pole configurations (FIG. 6B). Although not shown, it should be understood that storage of a pole configuration group in library 170 preferably includes the information used to form each pole configuration in the group (A, PW, F, location of poles, polarity of the poles and the current fraction they receive, etc.), as well as the relative position of each of the pole configurations to one another. As shown, library 170 can include pole configuration groups defined and saved by the user (option 163), and can also include pre-defined pole configuration groups. FIG. 13 shows several example of pre-defined pole configurations, which have various pole configurations (monopoles, bipoles, tripoles) used in various combinations and in various positions with respect to each other. As noted earlier, poles configurations in a group may overlap in space. This can be seen for example with respect to pre-defined pole configuration groups 7 and 13. Such overlapping in space is permissible, because as noted earlier the pulses in the pole configurations of a group preferably do not overlap in time (at least completely). User-defined or pre-defined pole configuration groups can be loaded for use in the GUI 64 using option 164 in FIG. 12.

A pole configuration group once defined may be modified in various ways, and an option 175 is included in FIG. 12 for this purpose. Once this option is selected, and as shown in FIG. 14, the user is given options to adjust various aspects of the pole configuration group. Option 180 displays the currently-selected pole configuration group for clarity (PCG cde in this example). Option 182 allows the pole configurations included in the group to be changed. For example, option 182 displays the various pole configurations available for use (again a-e), and shows the pole configurations (c-e) currently used in the selected group. For those pole configuration, options are provided to delete them from the group, i.e., any of c, d, or e can be deleted from PCG cde. Pole configurations not currently included in the selected pole configuration group can be added to the group, i.e., a and/or b can be added to PCG cde. Once these and other changes are made to a pole configuration group, the changes can be (re)saved using option 184, which will store the modified pole configuration group in library 170 (FIG. 13) as described earlier.

Note that pole configuration group modification aspect 175 can include aspect 150 described earlier, allowing any of the pole configurations in the selected group to be modified. Further, aspect 175 can specifically allow the positions of pole configurations linked in the group to be modified, such as is provided by option 190. In FIG. 14, the user has selected this option 190, and has used it to move the position of pole configuration (monopole) e relative to the positions of pole configurations c and d present in the group. Movement of pole configuration e can again use dial 112 or other means, such as by manipulating pole configuration e in the leads interface 168. Similarly, any of the linked pole configurations in the group can be rotated (166). Again, once the pole configuration group has been modified, it can be (re)saved using option 184.

Option 192 allows the user to review or adjust the timing at which pulses are issued in the pole configuration group. For example, selection of option 192 may graph in the GUI 64 the waveforms as they will be issued in the group, akin to what was shown earlier in FIG. 10. The GUI 64 may also allow the user the option to change the timing. For example, the user could decide to make time ta smaller and tb larger to issue the pulses in bipole 100b closer in time after the end of the pulses in bipole 100a. The user could also make timing adjustments to allow the pulses in the different pole configurations to overlap to some degree.

Definition, use, and modification of pole configuration groups is expected to be of significant benefit when used with the techniques disclosed in U.S. Pat. No. 10,576,282 (the '282 patent). The '282 patent teaches that a pole configuration can provide either supra-perception or sub-perception stimulation. Supra-perception stimulation generally causes paresthesia that a patient can feel. Paresthesia can be perceived by patients differently, but is often described as a tingling, prickling, or hot or cold sensation. Generally, the effects of paresthesia are mild, or at least are not overly concerning to a patient.

Especially in patients who find paresthesia disturbing, sub-perception stimulation can be used which is not felt by patients. Sub-perception therapy may provide pain relief without paresthesia in one example by issuing stimulation pulses at higher frequencies. Unfortunately, such higher-frequency stimulation may require more power, which tends to drain the battery 14 of the IPG 10 or ETS 40. See, e.g., U.S. Pat. No. 9,867,994. The '282 patent reports that effective sub-perception therapy can occur using lower frequencies, as discussed further below. However, sub-perception therapy can take some time to "wash in" before it is effective, meaning that a pole configuration may need to be remain at a particular location before it is moved during sweet spot searching. See, e.g., U.S. Pat. No. 11,160,987. Sub-perception therapy can be achieved by titrating the amplitude A of the bipole 100 until it is no longer felt by the patient.

The '282 patent discloses that sweet spot searching can therefore preferably occur using supra-perception stimulation, even if the resulting stimulation therapy to be provided following sweet spot searching is sub-perception. Supra-perception therapy by definition allows the patient to feel the stimulation, which enables the patient during sweet spot searching to provide essentially immediate feedback to the clinician whether the paresthesia seems to be well covering his pain without the need for a wash-in period. Further, use of supra-perception stimulation during sweet spot searching ensures that electrodes are determined that well recruit the neural site of a patient's pain. As a result, after the sweet spot search is complete and eventual sub-perception therapy is provided at the determined electrodes, wash in of that sub-perception therapy may not take as long because the electrodes needed for good recruitment have already been confidently determined.

The '282 patent explains that once the sweet spot searching has been completed and electrodes proximate to the patient's pain site 100 have been determined, sub-perception therapy can then be provided to the patient using those electrodes (or electrode close to them). Significantly, the '282 patent discloses that effective sub-perception therapy can occur even at lower frequencies (less than or equal to 10 kHz) that use lower amounts of power in the IPG 10 or ETS 40, and that effectiveness at such lower frequencies is achieved when the pulse widths are adjusted to certain values at each frequency. Graphs taken from the '282 patent are shown in FIG. 10, which shows the relationship between such lower frequencies and pulse widths noticed to provide optimal sub-perception therapy based on empirical testing. The '282 patent analyzes this data in more depth, including identifying particular relationships (curve fitting) and frequency/pulse width regions indicative of sub-perception effectiveness. The reader is assumed familiar with the '282 patent, and such details are thus not repeated here.

As applied to the current technique, a first pole configuration can be used during supra-perception sweet spot searching to find a first position in the electrode array 17 or 17' that seems to be addressing a patient's symptoms. At that point, a multiple pole configuration group can be defined and used proximate to that first position. For example, at least one other pole configuration can be added, with the GUI including an option to allow the user to specify the position of the second pole configuration relative to the first position. Thereafter, the group can be steered in unison to see if therapy can be further improved. If necessary, the pole configurations in the group can be titrated to sub-perception levels, and preferably applied to the patient at lower frequencies at appropriate corresponding pulse widths, as disclosed in the '282 patent. Sweet spot searching itself may occur using the frequencies/pulse width relationships disclosed in the '282 patent.

Various aspects of the disclosed techniques, including software 66 implemented in the external device (e.g., clinician programmer or external controller) to render and operate the GUI 64 and to formulate the stimulation that the IPG or ETS will receive, can be stored as instructions in a non-transitory computer-readable media, such as in a magnetic, optical, or solid state memory in the external device. The computer-readable media with such stored instructions may also comprise a device readable by the external device, such as in a memory stick or a removable disk, and may reside elsewhere. For example, the computer-readable media may be associated with a server or any other computer device, thus allowing instructions to be downloaded to the external device via the Internet for example.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system, comprising:
  a stimulator device comprising a plurality of electrodes forming an electrode array; and
  a non-transitory computer readable medium including instructions that, when executed on an external device, are configured to cause the external device to:
    render a Graphical User Interface (GUI) on the external device,
    allow a user to specify in the GUI a first pole configuration configured to provide stimulation at a first position relative to the electrode array,
    allow a user to specify in the GUI a second pole configuration configured to provide stimulation at a second position relative to the electrode array, wherein the GUI allows the user to link the first and second pole configurations together as a controllable group, and
    enable the stimulator device to concurrently apply the stimulation from the first and second pole configurations at the respective first and second positions in the electrode array.

2. The system of claim 1, wherein the instructions, when executed, are configured to allow the user via the GUI to create a single movement instruction configured to simultaneously move the first and second positions of the first and second pole configurations in the group in the electrode array.

3. The system of claim 2, wherein the instructions, when executed, are configured to provide one or more inputs to the GUI, wherein each of the one or more inputs is individually selectable by a user to create the single movement instruction.

4. The system of claim 2, wherein the instructions, when executed, are configured to provide a plurality of inputs to the GUI, wherein a user may select a plurality of the inputs to create the single movement instruction.

5. The system of claim 2, wherein the single movement instruction is configured to simultaneously move the positions of the linked two or more pole configurations in the same direction and the same distance in the electrode array.

6. The system of claim 2, wherein the single movement instruction is configured to simultaneously move the positions of the linked two or more pole configurations rotationally in the electrode array.

7. The system of claim 1, wherein the instructions, when executed, are configured to provide one or more inputs to the GUI to allow a user to adjust the second position relative to the first position.

8. The system of claim 1, wherein each of the first and second pole configuration comprises at least one anode pole and at least one cathode pole capable of forming an electric field in the patient's tissue.

9. The system of claim 8, wherein in at least some of the first and second pole configurations, the at least one anode pole, the at least one cathode pole, or both, are located at physical positions of the electrodes in the electrode array.

10. The system of claim 8, wherein in at least some of the first and second pole configurations, the at least one anode pole, the at least one cathode pole, or both, are not located at physical positions of the electrodes in the electrode array.

11. The system of claim 8, wherein in at least some of the first and second pole configurations, the at least one anode pole and the at least one cathode pole are formed in the electrode array.

12. The system of claim 1, wherein the stimulator device comprises a conductive case, wherein at least some of the first and second pole configurations comprise a single anode pole or a single cathode pole formed in the electrode array, and wherein in those at least some pole configurations the conductive case comprises the other of the anode pole or the cathode pole.

13. The system of claim 1, wherein each pole configuration provides stimulation in the electrode array as a sequence of pulses.

14. The system of claim 13, wherein the instructions, when executed, are further configured to cause the external device to cause the stimulator device to apply the stimulation from the first and second pole configurations concurrently such that the pulses of the pole configurations in the group do not completely overlap each other in time.

15. The system of claim 13, wherein the instructions, when executed, are further configured to cause the external device to cause the stimulator device to apply the stimulation from the first and second pole configurations concurrently such that the pulses of the pole configurations in the group do not overlap each other at any time.

16. The system of claim 1, wherein the first and second pole configurations physically overlap in the electrode array.

17. The system of claim 1, wherein the non-transitory computer readable medium further comprises a library, wherein the library is configured to store the first and second pole configurations, wherein the instructions, when executed, are configured to allow the user to specify the first and second pole configurations by loading them from the library using the GUI.

18. The system of claim 1, wherein the non-transitory computer readable medium further comprises a library, wherein the instructions, when executed, are further configured to allow the user to store the group of first and second pole configurations.

19. The system of claim 1, wherein the stimulator device comprises timing channel circuitry configured to support a plurality of timing channels, wherein the instructions, when executed, are further configured to cause the external device to allow a user to specify in the GUI the first pole configuration in a first of the timing channels, and to allow a user to specify in the GUI the second pole configuration in a second of the timing channels.

20. The system of claim 19, wherein the instructions, when executed, are further configured to cause the external device to enable the stimulator device to concurrently apply the stimulation from the first and second pole configurations using the first and second timing channels.

* * * * *